USOO5710123A

United States Patent [19]

Heavner et al.

[11] Patent Number: 5,710,123
[45] Date of Patent: Jan. 20, 1998

[54] PEPTIDE INHIBITORS OF SELECTIN BINDING

[75] Inventors: George A. Heavner, Malvern; Marian Kruszynski, King of Prussia, both of Pa.

[73] Assignee: Centocor, Inc., Malvern, Pa.

[21] Appl. No.: 454,207

[22] PCT Filed: Dec. 13, 1993

[86] PCT No.: PCT/US93/12110

§ 371 Date: Jun. 9, 1995

§ 102(e) Date: Jun. 9, 1995

[87] PCT Pub. No.: WO94/14836

PCT Pub. Date: Jul. 7, 1994

Related U.S. Application Data

[63] Continuation-in-part of Ser. No. 997,771, Dec. 18, 1992, abandoned.

[51] Int. Cl.$^6$ .............................. A01N 37/18; A61K 38/00; C07K 5/00; C07K 7/00
[52] U.S. Cl. ........................... 514/2; 514/9; 514/15; 530/300; 530/317; 530/321; 530/328; 530/333; 530/334
[58] Field of Search ................. 514/2, 9, 15; 530/300, 530/317, 321, 328, 333, 334

[56] References Cited

U.S. PATENT DOCUMENTS

| 3,625,214 | 12/1971 | Higuchi | 128/260 |
|---|---|---|---|
| 4,789,734 | 12/1988 | Pierschbacher | 530/395 |
| 4,906,474 | 3/1990 | Langer et al. | 424/428 |
| 4,925,673 | 5/1990 | Steiner et al. | 424/455 |
| 5,116,964 | 5/1992 | Capon et al. | 536/27 |
| 5,192,746 | 3/1993 | Lobl et al. | 514/11 |
| 5,198,424 | 3/1993 | McEver | 514/13 |
| 5,440,015 | 8/1995 | Macher et al. | 530/329 |
| 5,444,050 | 8/1995 | Kogan et al. | 514/25 |
| 5,464,935 | 11/1995 | Heavner et al. | 530/329 |
| 5,602,230 | 2/1997 | Heavner et al. | 530/327 |
| 5,618,785 | 4/1997 | Heavner et al. | 514/2 |

FOREIGN PATENT DOCUMENTS

| WO 91/07993 | 6/1991 | WIPO. |
|---|---|---|
| WO 91/19501 | 12/1991 | WIPO. |
| WO 91/19502 | 12/1991 | WIPO. |
| WO 92/01718 | 2/1992 | WIPO. |
| WO 92/02527 | 2/1992 | WIPO. |

OTHER PUBLICATIONS

Abbott, S.E. et al., "Isolation and culture of synovial microvascular endothelial cells", *Arthritis and Rheumatism* 1992, 35(4), 401–406.

Ager, A. and Humphries, M.J., "Use of synthetic peptides to probe lymphocyte– high endothelial cell interactions. Lymphocytes recognize a ligand on the endothelial surface which contains the CS1 adhesion motif", *International Immunology* 1990, 2 (10), 921–928.

Albelda, S.A. and Buck, C.A., "Integrins and other cell adhesion molecules", *FASEB* 1990, 4, 2868–2880.

Albelda, S.A., "Endothelial and epithelial cell adhesion molecules", *Am. J. Respir. Cell Mol. Biol.* 1991, 4, 195–203.

Aruffo, A. et al., "CD62/P–selectin recognition of myeloid and tumor cell sulfatides", *Cell* 1991, 67, 35–44.

Aruffo, A. et al., "Granule membrane protein 140 (GMP140) binds to carcinomas and carcinoma–derived cell lines", *PNAS USA* 1992, 89, 2292–2296.

Ball, G.E. et al., "Synthesis and structural analysis using 2–D NMR of sialyl Lewis X (SLe$^x$) and Lewis Le$^x$) oligosaccharides: ligands related to E–selectin [ELAM–1] binding", *American Chemical Society* 1992, 114, 5449–5451.

Bennett, J.S., "The molecular biology of platelet membrane proteins", *Seminars in Hematology* 1990, 27(2), 186–204.

Berg, M. and James, S.P., "human neutrophils release the leu–8 lymph node homing receptor during cell activation", *Blood* 1990, 76(11), 2381–2388.

Berg, E.L. et al., "A carbohydrate domain common to both Sialyl Le$^a$ and Sialyl Le$^x$ is recognized by the endothelial cell leukocyte adhesion molecule ELAM–1", *J. of Biological Research Communications* 1992, 266 (23), 14869–14872.

Berg, E.L. et al., "Comparison of L–selectin and E–selectin ligand specificities: the L–selectin can bind the E–selectin ligands SIALYL Le$^x$ and SIALYL Le$^a$", *Biochemical and Biophysical Research Communications* 1992, 184 (2), 1048–1055.

Bevilacqua, M. et al., "Endothelial leukocyte adhesion molecule 1: An inducible receptor for neutrophils related to complement regulatory proteins and lectins", *Science* 1989, 243, 1160–1165.

Bevilacqua, M. et al., "Selectins: a family of adhesion receptors", *Cell* 1991, 67, 233.

Bevilacqua, M. et al., "Identification of an inducible endothelial–leukocyte adhesion molecule", *Proc. Natl. Acad. Sci. USA* 1987, 84: 9238–9242.

Bodanszky, M. et al., "Peptide Synthesis", 2nd edition, John Wiley & Sons, 1976.

Bradley, L.M. et al., "Long–term CD4$^+$ memory T cells fron the spleen lack mel–14, the lynmph node homing receptor", *J. of Immunology* 1992, 148(2), 324–331.

Brandley, B.K. et al., "Carbohydrate ligands of the LE cell adhesion molecules", *Cell* 1990, 63, 861–863.

Brown, E. et al., "Integrin–associated protein: a 50–kD plasma membrane antigen physically and functionally associated with integrins", *J. of Cell Biology* 1990, 111 (6), 2785–2794.

(List continued on next page.)

Primary Examiner—W. Gary Jones
Assistant Examiner—Amy Atzel
Attorney, Agent, or Firm—Woodcock Washburn Kurtz Mackiewicz & Norris LLP

[57] ABSTRACT

The present invention provides novel peptides having as their core region portions of the 109–118 amino acid sequence of P-selectin, E-selectin or L-selectin. The invention also provides pharmaceutical compositions comprising the peptides of the invention, and diagnostic and therapeutic methods utilizing the peptides and pharmaceutical compositions of the invention.

23 Claims, No Drawings

OTHER PUBLICATIONS

Bührer, C. et al., "Lymphocyte activation and regulation of three adhesion molecules with supposed function in homing: LECAM-1 (MEL-14 Antigen), LPAM-1/2 ($\alpha^4$-integrin) and CD44 (Pgp-1)", *Scandinavian J. of Immunology* 1992, 35, 107–120.

Camerini, D. et al., "Leu-8/TQ1 is the human equivalent of the Mel-14 lymph node homing receptor", *Nature* 1989, 342, 78–82.

Carmody, M.W. et al., "Production of monoclonal antibodies secific for platelet activation antigens and their use in evaluating platelet function", *Hybridoma* 1990, 9(6), 631–641.

Celi, A. et al., "PADGEM: an adhesion receptor for leukocytes on stimulated platelets and endothelial cells", *Procedures of the Society of Experimental and Biological Medicine* 1991, 198(2), 703–709.

Corral, L. et al., "Requirement for Sialic acid on neutrophils in a GMP-140 (PADGEM) mediated adhesive interaction with activated platelets", *Biochemical and Biophysical Research Communications* 1990, 172(3), 1349–1356.

Damle, N.K. et al., "GMP-140 (P-selectin/cD62) binds to chronically stimulated but not resting CD4$^+$ T lymphocytes and regulates their production of proinflammatory cytokines", *European J. of Immunology* 1992, 22, 1789–1793.

de Bruijne–Admiraal, L.G. et al., "P-selectin mediates Ca$^{2+}$–dependent adhesion of activated platelets to many different types of leukocytes: detection by flow cytometry", *Blood* 1992, 80 (1), 134–142.

Dejana, E. et al., "Endothelial leukocyte adhesion molecule-1–dependent adhesion of colon carcinoma cells to vascular endothelium is inhibited by an antibody to Lewis fucosylated type 1 carbohydrate chain", *Laboratory Investigation* 1992, 66(3), 324–330.

Disdier, M. et al., "Cytoplasmic domain of p-selectin (CD62) contains the signal for sorting into the regulated secretory pathway", *Molecular Biology of the Cell* 1992, 3, 309–321.

Dunlop, L.C. et al., "Characterization of GMP-140(P-selectin) as a circulating plasma protein", *J. Exp. Med.* 1992, 175, 1147–1150.

Edgington, S.M., "How sweet it is: Selectin–mediating drugs", *Bio/Technology* 1992, 10, 383–389.

Erban, J.K. and Wagner, D.D., "A 130–kDa protein on endothelial cells binds to amino acids 15–42 of the B$\beta$ chain of fibrinogen", *J. of Biological Chemistry* 1992, 267(4), 2451–2458.

Feizi, T., "Carbohydrate differentiationn antigens: probable ligands for cell adhesion molecules", 1991, *Elsevier Science Publishers Ltd.* (UK), 84–86.

Fisher, M/A. and Malik, A.B., "Interactions between neutrophils and endothelial cells mediate lung vascular injury", *Applied Cardiopulmonary Pathophysiology* 1991, 4, 175–189, Foxall, C. et al., "The three members of the selectin receptor family recognize a common carbohydrate epitope, the sialyl Lewis$^x$ oligosaccharide", *J. of Cell Biology* 1992, 117(4), 895–902.

Furie, B. et al., "PADGEM, a leukocyte receptor on activated platelets", *Current Studies in Hematology Blood Transf.* 1991, 58, 32–36.

Furie, M.B. et al., "E–selectin (endothelial–leukocyte adhesion molecule–1) is not required for the migration of neutrophils across IL–1 stimulated endothelium in vitro", *J. of immunology* 1992, 148(8), 2395–2404.

Gamble, J.R. et al., "prevention of activated neutrophil adhesion to endothelium by soluble adhesion protein GMP-140", *Science* 1990, 249, 414–416.

Geng, J. et al., "Rapid neutrophil adhesion to activated endothelium mediated by GMP-140", *Nature* 1990, 343, 757–760.

Geng, J. et al., "Neutrophil recognition requires a Ca$^{2+}$–induced conformational change in the lectin domain of GMP-140", *J. of Biological Chemistry* 1991, 266(33), 22313–22319.

Gregoriadis, G. "Liposomes", Chap. 14 in Drug Carriers in Biology and Medicine, pp. 287–341, Academic Press, 1979.

Groves, R.W. et al., "Endothelial leucocyte adhesion molecule–1 (ELAM–1) expression in cutaneous inflammation", *British J. of Dermatology* 1991, 124, 117–123.

Hakkert, B.C. et al., "Neutrophil and monocyte adherence to and migration across monolayers of cytokine–activated endothelial cells: the contribution of CD18, ELAM–1, and VLA–4", *Blood* 1991, 78(10), 2721–2726.

Hamann, A. et al., "Homing reexamined: mouse LECAM–1 (MEL–14 antigen) is involved in lymphocyte migration into gut–associated lymphoid tissue", *Eur. J. Immunol.* 1991, 21, 2925–2929.

Hamburger, S.A. and McEver, R.P., "GMP–140 mediates adhesion of stimulated plateltes to neutrophils", *Blood* 1990, 75(3), 550–554.

Handa, K. et al., "Selectin GMP–140 (CD62; PADGEM) binds to sialosyl–Le$^a$ and sialosyl–Le$^x$, and sulfated glycans modulate this binding", *Biochemical and Biophysical Research Communications* 1991, 181(3), 1223–1230.

Handa, K. et al., "Downregulation of GMP–140 (CD62 or PADGEM) expressin on plateltes by N, N–dimethyl and N,N,N–trimethyl derivatives of sphingosine", *Biochemistry* 1991, 30, 11682–11686.

Harrison, F.L., "Soluble vertebrate lectins: ubiquitous but inscrutable proteins", *J. of Cell Science* 1991, 100, 9–14.

Hattori, R. et al., "Stimulated secretion of endothelial von Willebrand factor is accompanied by rapid redistribution to the cell surface of the intracellular granule membrane protein GMP–140", *J. of Biol. Chem.* 1989, 264, 7768–7771.

Huang, K. et al., "A lymphocyte homing receptor (1–selectin) mediates the in vitro attachment of lymphocytes to myelinated tracts of the central nervous system", *J. of Clinical Investigation* 1991, 88, 1778–1783.

Israels, S.J. et al., "Platelet dense granule membranes contain both granulophysin and P–selectin (GMP–140)", *Blood* 1992, 80 (1), 143–152.

Issekutz, A.C. et al., "Role of neutrophils in the deposition of platelets during acute inflammation", *Lab. Invest.* 1983, 49 (6), 716–724.

James, S.P. et al., "Multiple roles of Leu–8/MEL–14 in leukocyte adhesion and function", *Immunology Research* 1991, 10, 282–292.

Johnston, G.I. et al., "Structure of the human gene encoding granule membrane protein–140, a member of the selectin family of adhesion receptors for leukocytes", *J. of Biological Chemistry* 1990, 265(34), 21381–21385.

Johnston, G.I. et al., "Cloning of GMP–140, a granule membrane protein of platelets and endothelium: sequence similarity to proteins involved in cell adhesion and inflammation", *Cell* 1989, 56, 1033–1044.

Jutila, M.A. et al., "Leukocyte traffic to sites of inflammation", *APMIS* 1992, 100, 191–201.

Jutila, M.A. et al., "function and regulation of the neutrophil MEL–14 antigen in vivo: comparison with LFA–1 and MAC–1", *J. of Immunology* 1989, 143(10), 3318–3324.

Kansas, G.S., "Structure and function of L–selectin", *APMIS,* 1992, 100, 287–293.

Karlsson, K.A., "Glycobiology: a growing field for drug design", *TIPS* 1991, 12, 265–272.

Kitagawa, H. et al., "Characterization of mucin–type oligosaccharides with the sialyl-Le$^a$ structure from human colorectal adenocarcinoma", *Biochemical and Biophysical Research communications* 1991, 178(3), 1429–1436.

Knapp, W. et al., "Antibody–defined cell surface molecules of the immune system", *Current Opinion in Immunology* 1990, 2, 884–891.

Koedam, J.A. et al., "P–selectin, a granule membrane protein of plateltes and endothelial cells, follows the regulated secretory pathway in AtT–20 cells", *J. of Cell Biology* 1992, 116(3), 617–625.

Kojima, N. et al., "Inhibition of selectin–dependent tumor cell adhesion to endothelial cells and platelets by blocking o–glycosylation of these cells", *Biochemical and Biophysical Research Communications* 1992, 182(3), 1288–1295.

Kuijpers, T.W. et al., "Role of endothelial leukocyte adhesion molecule–1 and platelet–activationg factor in neutrophil adherence to IL–1 prestimulated endothelial cells", *J. of Immunology* 1991, 147(4), 1369–1376.

Larkin, M. et al., "Spectrum of sialylated and nonsialylated fuco–olifosaccharides bound by the endothelial–leukocyte adhesion molecule E–selectin", *J. of Biological Chemistry* 1992, 267(19), 13661–13668.

Larsen, E. et al., "PADGEM protein: a receptor that mediates the interaction of activated platelets with neutrophils and monocytes", *Cell* 1989, 59, 305–312.

Larsen, E. et al., "PADGEM–dependent adhesion of platelets to monocytes and neutrophils is mediated by a lineage–specific carbohydrate, LNF III (CD15)", *Cell* 1990, 63, 467–474.

Lasky, L.A. et al., "An endothelial ligand for L–selectin is a novel mucin–like molecule", *Cell* 1992, 69, 927–938.

Lasky, L.A. et al., "Cloning of a lymphocyte homing receptor reveals a lectin domain", *Cell* 1989, 56, 1045–1055.

Lawrence, M.B. et al., "Leukocytes roll on a selectin at physiologic flow rates: distinction from and prerequisite for adhesion through integrins", *Cell* 1991, 65, 859–873.

Leeuwenberg, J.F.M. et al., "The ligand recognized by ELAM–1 on HL60 cells is not carried by N–linked oligosaccharides", *Eur. J. Immunol.* 1991, 21, 3057–3059.

Leeuwenberg, J.F.M. et al., "Adhesion of polymorphonuclear cells to human endothelial cells. adhesion–molecule–dependent, and Fc receptor–mediated adhesion–molecule–independent mechanisms", *Clin. exp. Immunol.* 1990, 81, 496–500.

Leeuwenberg, J.F.M. et al., "Role of ELAM–1 in adhesion of monocytes to activated human endothelial cells", *Scandinavian J. of Immunology* 1992, 35, 335–341.

Ley, K. et al., "Shear dependent inhibition of granulocyte adhesion to cultured endothelium by dextran sulfate", *Blood* 1989, 73(5), 1324–1330.

Lin, Y. et al., "Conformational studies os sialyl Lewis X in aqueous solution", *J. of American Chemical Society* 1992, 114, 5452–5454.

Lobb, R.R. et al., "Expression and functional characterization of soluble form of endothelial–leukocyte adhesion molecule 1", *J. of Immunology* 1991, 147(1), 124–129.

Lorant, D.E. et al., "Coexpression of GMP–140 and PAF by endothelium stimulated by histamine or thrombin: a juxtacrine system for adhesion and activation of neutrophils", *J. of Cell Biology* 1991, 115(1), 223–234.

Lowe, J.B. et al., "ELAM–1–dependent cell adhesion to vascular endothelium determined by a transfected human fucosyltransferase cDNA", *Cell* 1990, 63, 475–484.

Lowe, J.B. et al., "A transfected human fucosyltransferase cDNA determines biosynthesis of oligosaccharide ligand(s) for endothelial–leukocyte adhesion molecule I", *Biochemical Society Transactions* 1991, 19(3), 649–653.

Majuri, M.L. et al., "Recombinant E–selectin–protein mediates tumor cell adhesion via sialyl–Lea and sialyl–Lex", *Biochemical and Biophysical Research Communications* 1992, 182(3), 1376–1382.

May, G.L. et al., "GMP–140(P–selectin inhibits human neutrophil activation by lipopolysaccharide spectroscopy", *Biochemical and Biophysical Research Communications* 1992, 183(3), 1062–1069.

McEver, R.P., "Leukocyte interactions mediated by selectins", *Thrombosis and Haemostasis* 1991, 66(1), 80–87.

McEver, R.P., "GMP–140, a receptor that mediates interactions of leukocytes with activated platelets and endothelium", *TCM* 1991, 1(4), 152–156.

McEver, R.P. et al., "GMP–140, a platelet α–granule membrane protein, is also synthesized by vascular endothelial cells and is localized in weibel–palade bodies", *J. Clin. Invest.* 1989, 84, 92–99.

McEver, R.P., "Selectins: Novel receptors that mediate leukocyte adhesion during inflammation", *Thrombosis and Haemostasis* 1990, 65(3), 223–228.

McEver, R.P., "GMP–140: a receptor for neutrophils and monocytes on activated platelets and endothelium", *J. of Cellular Biochemistry* 1991, 45, 156–161.

McEver, R.P. et al., "The platelet α–granule membrane protein GMP–140 is also synthesized by human vascular endothelial cells and is present in blood vessels of diverse tissues", *Blood* 1987, 70(5) Suppl.1, 355a, Abstract No. 1274.

McEver, R.P. and Martin, M.N., "A monoclonal antibody to a membrane glycoprotein binds only to activated platelets", *J. of Biol. Chem.* 1984, 259(15), 9799–9804.

Merrifield, R.B., "Solid Phase Peptide Synthesis. I. The Synthesis of a Tetrapeptide", *J. Am. Chem. Soc.* 1963, 85, 2149–2154.

Metzelaar, M.J. et al., "Biochemical and immunohistochemical characteristics of CD62 and CD63 monoclonal antibodies", *Virchows Archives B Cell Pathology* 1991, 61, 269–277.

Montefort, S. and Holgate, S.T., "Adhesion molecules and their role in inflammation", *Respiratory Medicine* 1991, 85, 91–99.

Moore, K.L. et al., "GMP–140 binds to a glycoprotein receptor on human neutrophils: evidence for a lectin–like interaction", *J. of Cell Biol.* 1991, 112, 491–499.

Müller–Eberhard, H.J., "Molecular organization and function of the complement system", *Ann. Rev. Biochem.* 1988, 57, 321–347.

Mulligan, M.S. et al., "Role of endothelial–leukocyte adhesion molecule 1 (ELAM–1) in neutrophil–mediated lung injury in rats", *J. Clin. Invest.* 1991, 88, 1396–1406.

Norton, J. et al., "Expression of adhesion molecules in human intestinal graft-versus-host disease", *Clin. Exp. Immunol.* 1992, 87, 231–236.

Ord, D.C. et al., "Structure of the gene encoding the human leukocyte adhesion molecule-1 (TQ1, Leu-8) of lymphocytes and neutrophils", *J. of Biological Chemistry* 1990, 265(14), 7760–7767.

Osborn, L., "Leukocyte adhesion to endothelium in inflammation", *Cell* 1990, 62, 3–6.

Parish, C.R. et al., "Carbohydrate recognition molecules on lymphocytes", *Biochem. Soc. Trans.* 1992, 20(2), 295–297.

Parmentier, S. et al., "Inhibition of platelet function by a monoclonal antibody (LYP20) directed against a granule membrane glycoprotein (GMP-140/PADGEM)", *Blood* 1991, 77(8), 1734–1739.

Parmentier, S. et al., "A new family of cell–cell adhsion molecules: ELAM-1, GP90 $^{MEL-14}$ and GMP-140", *Fundamental and Clinical Aspects* 1991, 206, 63–73.

Parmentier, S. et al., "New families of adhesion molecules play a vital role in platelet functions", *Immunology Today* 1990, 11(7).

Patarroyo, M., "Short analytical review: Leukocyte adhesion in host defense and tissue injury", *Clinical Immunology and Immunopathology* 1991, 60, 333–348.

Picker, L.J. et al., "The neutrophil selectin LECAM-1 presents carbohydrate ligands to the vascular selectins ELAM-1 and GMP-140", *Cell* 1991, 66, 921–933.

Pigott, R. et al., "Structural and functional studies of the endothelial activation antigen endothelial leucocyte adhesion molecule-1 using a panel of monoclonal antibodies", *J. of Immunology* 1991, 147(1), 130–135.

Pober, J.S. and Cotran, R.S., "What can be learned from the expression of endothelial adhesion molecules in tissues", *Laboratory Investigation* 1991, 64(3), 301–305.

Pober, J.S. and Cotran, R.S., "The role of endothelial cells in inflammation", *Transplantation* 1990, 50(4), 537–544.

Postigo, A.A. et al., "Increased binding of synovial t lumphocytes from rheumatoid arthritis to endothelial–leukocyte adhesion molecule-1 (ELAM-1) and vascular cell adhesion molecule-1 (VCAM-1)", *J. of Clinical Investigation* 1992, 89, 1445–1452.

Rinder, H.M. et al., "Dynamics of leukocyte–platelet adhesion in whole blood", *Blood* 1991, 78(7), 1730–1737.

Rinder, H.M. et al., "Activated and unactivated platelet adhesion to monocytes and neutrophils", *Blood* 1991, 78(7), 1760–1769.

Romson, J.L. et al., "Reduction of the extent of ischemic myocardial injury by neutrophil depletion in the dog", *Circulation* 1983, 67, 1016–1023.

Ryan, U.S. and Worthington, R.E., "Cell–cell contact mechanisms", *Current Opinion in Immunology* 1992, 4, 33–37.

Shimizu, Y. et al., "Four molecular pathways of T cell adhesion to endothelial cells: roles of LFA-1, VCAM-1, and ELAM-1 and changes in pathway hierarchy under different activation conditions", *J. of Cell Biology* 1991, 113 (5), 1203–1212.

Shimizu, Y. et al., "Activation–independent binding of human memory T cells to adhesion molecule ELAM-1", *Nature* 1991, 349, 799–802.

Shipp, M. A. et al., "CD10 (CALLA) neutral endopeptidase 24.11 modulates inflammatory peptide–induced changes in neutrophil morphology, migration, and adhesion proteins and is itself regulated by newtrophil activation", *Blood* 1991, 78 (7), 1834–1841.

Siegelman, M.H. et al., "The mouse lymph node homing receptor is identical with the lymphocyte cell surface marker Ly-22: role of the EGF domain in endothelial binding", *Cell* 1990, 61, 611–622.

Skinner, M.P. et al., "GMP-140 binding to neutrophils inhibited by sulfated glycans", *J. of Biological Chemistry* 1991, 266(9), 5371–5374.

Smith, C.W., "Molecular determinants of neutrophil adhesion", *Am. J. Respir. Cell Mol. Biol.* 1990, 2, 487–489.

Smith, C.W., "PMN adhesion and extravasation as a paradigm for tumor cell dissemination", *Cancer and Metastasis Reviews* 1991, 10, 61–78.

Spertini, O. et al., "Monocyte attachment to activated human vascular endothelium in vitro is mediated by leukocyte adhesion molecule-1 (L–selectin) under nonstatic conditions", *J. Exp. Med.* 1992, 175, 1789–1792.

Spertini, O. et al., "Leukocyte adhesion molecule-1 (LAM-1, 1–selectin) interacts with an inducible endothelial cell ligand to support leukocyte adhesion", *J. of Immunology* 1991, 147(8), 2565–2573.

Springer, T.A. and Lasky, L.A., "Sticky sugars for selectins", *Nature* 1991, 349, 196–197.

Springer, T.A., "Adhesion receptors of the immune system", *Nature* 1990, 346, 425–434.

Stoolman, L.M., "Selectins (LEC-CAMs): Lectin-like receptors involved in lymphocyte recirculation and leukocyte recruitment", in *Cell surface Carbohydrates and Cell Development*, Fukuda, M. Ph.D., Ed., CRC Press, 71–98.

Swiedler, S.J., "Invited commentary to the glyco–forum", *Glycobiology* 1991, 1(3), 237–241.

Takada, A. et al., "Adhesion of human cancer cells to vascular endothelium mediated by a carbohydrate antigen, sialykl Lewis A", *Biochemical and Biophysical Research Communications* 1991, 179(2), 713–719.

Tedder, T.F. et al., "Isolation and chromosomal localization of cDNAs encoding a novel human lymphocyte cell surface molecule, LAM-1", *J. Exp. Med.* 1989, 170, 123–133.

Todoroki, N. et al., "Enhancement by IL-1β and IFN-τ of platelet activation: adhesion to leukocytes via GMP-140/PADGEM protein (CD62)", *Biochem. and Biophys. Res. Commun.* 1991, 179(2), 756–761.

Toothill, V.J. et al., "Characterization of the enhance adhesion of neutrophil leukocytes to thrombin–stimulated endothelial cells", *J. of Immunology* 1990, 145, 283–291.

True, D.D. et al., "Requirement for sialyl acid on the endothelial ligand of a lymphocyte homing receptor", *J. of Cell Biology* 1990, 111(6 pt.1), 2757–2764.

Tyrrell, D. et al., "Structural requirements for the carbohydrate ligan of E–selectin", *Proc. Natl. Acad. Sci. USA* 1991, 88, 10372–10376.

Vadas, M.A. and Gamble, J.R., "Regulation of the adhesion of neutrophils to endothelium", *Biochemical Pharmacology* 1990, 40(8), 1683–1687.

Volpes, R. et al., "Vascular adhesion molecules in acute and chronic liver inflammation", *Hepatology* 1992, 15(2), 269–275.

Walcheck, B. et al., "Characterization of the bovine peropheral lymph node homing recceptor: a lectin cell adhesion molecule (LECAM)", *Eur. J. Immunol.* 1992, 22, 469–476.

Watson, M.L. et al., "Genomic organization of the selectin family of leukocyte adhesion molecules on human and mouse chromosome 1", *J. Exp. Med.* 1990, 172, 263–272.

Watson, S. R. et al., "Neutrophil influx into an inflammatory site inhibited by a soluble homing receptor–IgG chimaera", *Nature* 1991, 349, 164–166.

Watson, S. R. et al., "The complement binding–like domains of the murine homing receptor facilitate lectin activity", *J. of Cell Biology* 1991, 115(1), 235–243.

Wautier, J. et al., "Symposium: Leukocyte adhesion—rheological, biophysiccal and pharmacological approaches", *Biorheology* 1990, 27, 425–432.

Winocour, P.D. et al., "A member of the selectin family (GMP–140/PADGEM) is expressed on thrombin–stimulated rat platelets in vitro", *Comp. Biochem. Physiol.* 1992, 102A(2), 265–271.

Wong, C.S. et al., "Adhesion protein GMP140 inhibits superoxide anion release by human neutrophils", *Proc. Natl. Acad. Sci. USA* 1991, 88, 2397–2401.

Yednock, T.A. and Rosen, S.D., "Lymphocyte homing", *Advances in Immunology* 1989, 44, 313–378.

Yong, K. and Khwaja, A., "Leuocyte cellular adhesion molecules", *Blood Reviews* 1990, 4, 21–225.

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
( A ) LENGTH: 10 amino acids
( B ) TYPE: amino acid
( D ) TOPOLOGY: linear ( x i ) SEQUENCE DESCRIPTION: SEQ ID NO:1:

```
Cys Leu Lys Lys Lys His Ala Leu Cys Tyr
 1               5                   10
```

( 2 ) INFORMATION FOR SEQ ID NO:2:

( i ) SEQUENCE CHARACTERISTICS:
( A ) LENGTH: 10 amino acids
( B ) TYPE: amino acid
( D ) TOPOLOGY: linear ( x i ) SEQUENCE DESCRIPTION: SEQ ID NO:2:

```
Cys Ser Lys Lys Lys Leu Ala Leu Cys Tyr
 1               5                   10
```

( 2 ) INFORMATION FOR SEQ ID NO:3:

( i ) SEQUENCE CHARACTERISTICS:
( A ) LENGTH: 10 amino acids (B) TYPE: amino acid
(D) TOPOLOGY: linear (xi) SEQUENCE DESCRIPTION: SEQ ID NO:3:

Cys His Lys Leu Lys Ala Ala Leu Cys Tyr
 1               5                   10

(2) INFORMATION FOR SEQ ID NO:4:

(i) SEQUENCE CHARACTERISTICS:
    (A) LENGTH: 10 amino acids
    (B) TYPE: amino acid
    (D) TOPOLOGY: circular (xi) SEQUENCE DESCRIPTION: SEQ ID NO:4:

Cys Leu Lys Lys Lys His Ala Leu Cys Tyr
 1               5                   10

(2) INFORMATION FOR SEQ ID NO:5:

(i) SEQUENCE CHARACTERISTICS:
    (A) LENGTH: 10 amino acids
    (B) TYPE: amino acid
    (D) TOPOLOGY: circular (xi) SEQUENCE DESCRIPTION: SEQ ID NO:5:

Cys Ser Lys Lys Lys Leu Ala Leu Cys Tyr
 1               5                   10

(2) INFORMATION FOR SEQ ID NO:6:

(i) SEQUENCE CHARACTERISTICS:
    (A) LENGTH: 10 amino acids
    (B) TYPE: amino acid
    (D) TOPOLOGY: circular (xi) SEQUENCE DESCRIPTION: SEQ ID NO:6:

Cys His Lys Leu Lys Ala Ala Leu Cys Tyr
 1               5                   10

(2) INFORMATION FOR SEQ ID NO:7:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:7:

Phe Lys Lys Lys Leu Ala Leu Cys Tyr
 1               5

(2) INFORMATION FOR SEQ ID NO:8:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:8:

Phe Lys Lys Lys Leu Ala Leu Cys Tyr
 1               5

(2) INFORMATION FOR SEQ ID NO:9:

(i) SEQUENCE CHARACTERISTICS:
    (A) LENGTH: 9 amino acids
    (B) TYPE: amino acid
    (D) TOPOLOGY: linear (xi) SEQUENCE DESCRIPTION: SEQ ID NO:9:

His Lys Lys Lys Leu Ala Leu Cys Tyr
1               5

(2) INFORMATION FOR SEQ ID NO:10:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:10:

His Lys Lys Lys Leu Ala Leu Cys Tyr
1               5                         10

(2) INFORMATION FOR SEQ ID NO:11:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:11:

Leu Lys Lys Lys His Ala Leu Cys Tyr
1               5

(2) INFORMATION FOR SEQ ID NO:12:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:12:

Leu Lys Lys Lys Leu Ala Leu Cys Tyr
1               5

(2) INFORMATION FOR SEQ ID NO:13:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:13:

Leu Lys Lys Lys Leu Ala Leu Cys Tyr
1               5

(2) INFORMATION FOR SEQ ID NO:14:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:14:

Asn Lys Lys Lys Leu Ala Leu Cys Tyr
1               5

(2) INFORMATION FOR SEQ ID NO:15:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:15:

```
        Asn  Lys  Lys  Lys  Leu  Ala  Leu  Cys  Tyr
         1                  5
```

(2) INFORMATION FOR SEQ ID NO:16:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:16:

```
        Pro  Lys  Lys  Lys  Leu  Ala  Leu  Cys  Tyr
         1                  5
```

(2) INFORMATION FOR SEQ ID NO:17:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:17:

```
        Gln  Lys  Lys  Lys  Leu  Ala  Leu  Cys  Tyr
         1                  5
```

(2) INFORMATION FOR SEQ ID NO:18:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:18:

```
        Ser  His  Lys  Lys  Leu  Ala  Leu  Cys  Tyr
         1                  5
```

(2) INFORMATION FOR SEQ ID NO:19:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:19:

```
        Ser  Lys  Ala  Lys  Leu  Ala  Leu  Cys  Tyr
         1                  5
```

(2) INFORMATION FOR SEQ ID NO:20:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:20:

```
        Ser  Lys  Phe  Lys  Leu  Ala  Leu  Cys  Tyr
         1                  5
```

(2) INFORMATION FOR SEQ ID NO:21:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:21:

```
        Ser  Lys  His  Lys  Leu  Ala  Leu  Cys  Tyr
```

(2) INFORMATION FOR SEQ ID NO:22:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:22:

Ser Lys Lys Phe Leu Ala Leu Cys Tyr
     1              5

(2) INFORMATION FOR SEQ ID NO:23:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:23:

Ser Lys Lys Lys Ala Ala Leu Cys Tyr
     1              5

(2) INFORMATION FOR SEQ ID NO:24:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:24:

Ser Lys Lys Lys Ala Ala Leu Cys Tyr
     1              5

(2) INFORMATION FOR SEQ ID NO:25:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:25:

Ser Lys Lys Lys His Ala Leu Cys Tyr
     1              5

(2) INFORMATION FOR SEQ ID NO:26:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:26:

Ser Lys Lys Lys Ile Ala Leu Cys Tyr
     1              5

(2) INFORMATION FOR SEQ ID NO:27:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:27:

Ser Lys Lys Lys Leu Ala Phe Cys Tyr
     1              5

( 2 ) INFORMATION FOR SEQ ID NO:28:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:28:

```
Ser  Lys  Lys  Lys  Leu  Ala  Ile  Cys  Tyr
 1                    5
```

( 2 ) INFORMATION FOR SEQ ID NO:29:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:29:

```
Ser  Lys  Lys  Lys  Leu  Ala  Leu  Cys  Phe
 1                    5
```

( 2 ) INFORMATION FOR SEQ ID NO:30:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:30:

```
Ser  Lys  Lys  Lys  Leu  Ala  Leu  Cys  Ile
 1                    5
```

( 2 ) INFORMATION FOR SEQ ID NO:31:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:31:

```
Ser  Lys  Lys  Lys  Leu  Ala  Leu  Cys  Tyr
 1                    5
```

( 2 ) INFORMATION FOR SEQ ID NO:32:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:32:

```
Ser  Lys  Lys  Lys  Leu  Ala  Leu  Phe  Tyr
 1                    5
```

( 2 ) INFORMATION FOR SEQ ID NO:33:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:33:

```
Ser  Lys  Lys  Lys  Leu  Ala  Leu  Ile  Val
 1                    5
```

( 2 ) INFORMATION FOR SEQ ID NO:34:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:34:

Ser Lys Lys Lys Leu Ala Leu Ile Tyr
1                   5

( 2 ) INFORMATION FOR SEQ ID NO:35:

( i ) SEQUENCE CHARACTERISTICS:
      ( A ) LENGTH: 9 amino acids
      ( B ) TYPE: amino acid
      ( D ) TOPOLOGY: linear ( x i ) SEQUENCE DESCRIPTION: SEQ ID NO:35:

Ser Lys Lys Lys Leu Ala Leu Ile Tyr
1                   5

( 2 ) INFORMATION FOR SEQ ID NO:36:

( i ) SEQUENCE CHARACTERISTICS:
      ( A ) LENGTH: 9 amino acids
      ( B ) TYPE: amino acid
      ( D ) TOPOLOGY: linear ( x i ) SEQUENCE DESCRIPTION: SEQ ID NO:36:

Ser Lys Lys Lys Leu Ala Leu His Tyr
1                   5

( 2 ) INFORMATION FOR SEQ ID NO:37:

( i ) SEQUENCE CHARACTERISTICS:
      ( A ) LENGTH: 9 amino acids
      ( B ) TYPE: amino acid
      ( D ) TOPOLOGY: linear ( x i ) SEQUENCE DESCRIPTION: SEQ ID NO:37:

Ser Lys Lys Lys Leu Ala Leu Leu Tyr
1                   5

( 2 ) INFORMATION FOR SEQ ID NO:38:

( i ) SEQUENCE CHARACTERISTICS:
      ( A ) LENGTH: 9 amino acids
      ( B ) TYPE: amino acid
      ( D ) TOPOLOGY: linear ( x i ) SEQUENCE DESCRIPTION: SEQ ID NO:38:

Ser Lys Lys Lys Leu Ala Leu Leu Tyr
1                   5

( 2 ) INFORMATION FOR SEQ ID NO:39:

( i ) SEQUENCE CHARACTERISTICS:
      ( A ) LENGTH: 9 amino acids
      ( B ) TYPE: amino acid
      ( D ) TOPOLOGY: linear ( x i ) SEQUENCE DESCRIPTION: SEQ ID NO:39:

Ser Lys Lys Lys Leu Ala Leu Val Tyr
1                   5

( 2 ) INFORMATION FOR SEQ ID NO:40:

( i ) SEQUENCE CHARACTERISTICS:

(A) LENGTH: 9 amino acids
(B) TYPE: amino acid
(D) TOPOLOGY: linear (xi) SEQUENCE DESCRIPTION: SEQ ID NO:40:

Ser Lys Lys Lys Leu Ala Leu Val Tyr
 1               5

(2) INFORMATION FOR SEQ ID NO:41:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:41:

Ser Lys Lys Lys Leu Ala Leu Thr Tyr
 1               5

(2) INFORMATION FOR SEQ ID NO:42:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:42:

Ser Lys Lys Lys Leu Ala Pro Cys Tyr
 1               5

(2) INFORMATION FOR SEQ ID NO:43:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:43:

Ser Lys Lys Lys Leu Phe Leu Cys Tyr
 1               5

(2) INFORMATION FOR SEQ ID NO:44:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:44:

Ser Lys Lys Lys Leu His Leu Cys Tyr
 1               5

(2) INFORMATION FOR SEQ ID NO:45:

(i) SEQUENCE CHARACTERISTICS:
      (A) LENGTH: 9 amino acids
      (B) TYPE: amino acid
      (D) TOPOLOGY: linear (xi) SEQUENCE DESCRIPTION: SEQ ID NO:45:

Ser Lys Lys Lys Leu Ile Leu Cys Tyr
 1               5

(2) INFORMATION FOR SEQ ID NO:46:

(i) SEQUENCE CHARACTERISTICS:
      (A) LENGTH: 9 amino acids
      (B) TYPE: amino acid (D) TOPOLOGY: linear (x i) SEQUENCE DESCRIPTION: SEQ ID NO:46:

Ser Lys Lys Lys Leu Gln Ala Cys Tyr
 1               5

(2) INFORMATION FOR SEQ ID NO:47:

(i) SEQUENCE CHARACTERISTICS:
    (A) LENGTH: 9 amino acids
    (B) TYPE: amino acid
    (D) TOPOLOGY: linear (x i) SEQUENCE DESCRIPTION: SEQ ID NO:47:

Ser Lys Lys Lys Thr Ala Leu Cys Tyr
 1               5

(2) INFORMATION FOR SEQ ID NO:48:

(i) SEQUENCE CHARACTERISTICS:
    (A) LENGTH: 9 amino acids
    (B) TYPE: amino acid
    (D) TOPOLOGY: linear (x i) SEQUENCE DESCRIPTION: SEQ ID NO:48:

Ser Lys Lys Gln Leu Ala Leu Cys Tyr
 1               5

(2) INFORMATION FOR SEQ ID NO:49:

(i) SEQUENCE CHARACTERISTICS:
    (A) LENGTH: 9 amino acids
    (B) TYPE: amino acid
    (D) TOPOLOGY: linear (x i) SEQUENCE DESCRIPTION: SEQ ID NO:49:

Ser Lys Lys Arg Leu Ala Leu Cys Tyr
 1               5

(2) INFORMATION FOR SEQ ID NO:50:

(i) SEQUENCE CHARACTERISTICS:
    (A) LENGTH: 9 amino acids
    (B) TYPE: amino acid
    (D) TOPOLOGY: linear (x i) SEQUENCE DESCRIPTION: SEQ ID NO:50:

Ser Lys Lys Arg Leu Ala Leu Cys Tyr
 1               5

(2) INFORMATION FOR SEQ ID NO:51:

(i) SEQUENCE CHARACTERISTICS:
    (A) LENGTH: 9 amino acids
    (B) TYPE: amino acid
    (D) TOPOLOGY: linear (x i) SEQUENCE DESCRIPTION: SEQ ID NO:51:

Ser Lys Leu Lys Leu Ala Leu Cys Tyr
 1               5

(2) INFORMATION FOR SEQ ID NO:52:

(i) SEQUENCE CHARACTERISTICS:
    (A) LENGTH: 9 amino acids
    (B) TYPE: amino acid
    (D) TOPOLOGY: linear ( x i ) SEQUENCE DESCRIPTION: SEQ ID NO:52:

Ser  Lys  Leu  Lys  Leu  Ala  Leu  Cys  Tyr
 1                  5

( 2 ) INFORMATION FOR SEQ ID NO:53:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:53:

Ser  Lys  Arg  Lys  Leu  Ala  Leu  Cys  Tyr
 1                  5

( 2 ) INFORMATION FOR SEQ ID NO:54:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:54:

Ser  Lys  Arg  Lys  Leu  Ala  Leu  Cys  Tyr
 1                  5

( 2 ) INFORMATION FOR SEQ ID NO:55:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:55:

Ser  Lys  Arg  Lys  Arg  Ala  Leu  Cys  Tyr
 1                  5

( 2 ) INFORMATION FOR SEQ ID NO:56:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:56:

Ser  Lys  Arg  Lys  Arg  Ala  Leu  Cys  Tyr
 1                  5

( 2 ) INFORMATION FOR SEQ ID NO:57:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:57:

Ser  Lys  Arg  Arg  Leu  Ala  Leu  Cys  Tyr
 1                  5

( 2 ) INFORMATION FOR SEQ ID NO:58:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:58:

Ser   Lys   Arg   Arg   Leu   Ala   Leu   Cys   Tyr
     1                       5

( 2 ) INFORMATION FOR SEQ ID NO:59:

( i ) SEQUENCE CHARACTERISTICS:
       ( A ) LENGTH: 9 amino acids
       ( B ) TYPE: amino acid
       ( D ) TOPOLOGY: linear ( x i ) SEQUENCE DESCRIPTION: SEQ ID NO:59:

Ser   Lys   Arg   Arg   Leu   Ala   Leu   Ser   Tyr
     1                       5

( 2 ) INFORMATION FOR SEQ ID NO:60:

( i ) SEQUENCE CHARACTERISTICS:
       ( A ) LENGTH: 9 amino acids
       ( B ) TYPE: amino acid
       ( D ) TOPOLOGY: linear ( x i ) SEQUENCE DESCRIPTION: SEQ ID NO:60:

Ser   Lys   Ser   Lys   Leu   Ala   Leu   Cys   Tyr
     1                       5

( 2 ) INFORMATION FOR SEQ ID NO:61:

( i ) SEQUENCE CHARACTERISTICS:
       ( A ) LENGTH: 9 amino acids
       ( B ) TYPE: amino acid
       ( D ) TOPOLOGY: linear ( x i ) SEQUENCE DESCRIPTION: SEQ ID NO:61:

Ser   Arg   Ala   Arg   Leu   Ala   Leu   Cys   Tyr
     1                       5

( 2 ) INFORMATION FOR SEQ ID NO:62:

( i ) SEQUENCE CHARACTERISTICS:
       ( A ) LENGTH: 9 amino acids
       ( B ) TYPE: amino acid
       ( D ) TOPOLOGY: linear ( x i ) SEQUENCE DESCRIPTION: SEQ ID NO:62:

Ser   Arg   Ala   Arg   Leu   Ala   Leu   Cys   Tyr
     1                       5

( 2 ) INFORMATION FOR SEQ ID NO:63:

( i ) SEQUENCE CHARACTERISTICS:
       ( A ) LENGTH: 9 amino acids
       ( B ) TYPE: amino acid
       ( D ) TOPOLOGY: linear ( x i ) SEQUENCE DESCRIPTION: SEQ ID NO:63:

Ser   Arg   Lys   Lys   Leu   Ala   Leu   Cys   Tyr
     1                       5

( 2 ) INFORMATION FOR SEQ ID NO:64:

( i ) SEQUENCE CHARACTERISTICS:
       ( A ) LENGTH: 9 amino acids
       ( B ) TYPE: amino acid
       ( D ) TOPOLOGY: linear ( x i ) SEQUENCE DESCRIPTION: SEQ ID NO:64:

Ser   Arg   Lys   Lys   Leu   Ala   Leu   Cys   Tyr
     1                       5

(2) INFORMATION FOR SEQ ID NO:65:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:65:

Ser Arg Lys Arg Leu Ala Leu Cys Tyr
     1                 5

(2) INFORMATION FOR SEQ ID NO:66:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:66:

Ser Arg Lys Arg Leu Ala Leu Cys Tyr
     1                 5

(2) INFORMATION FOR SEQ ID NO:67:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:67:

Ser Arg Lys Arg Leu Ala Leu Ser Tyr
     1                 5

(2) INFORMATION FOR SEQ ID NO:68:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:68:

Ser Arg Arg Lys Leu Ala Leu Cys Tyr
     1                 5

(2) INFORMATION FOR SEQ ID NO:69:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:69:

Ser Arg Arg Lys Leu Ala Leu Cys Tyr
     1                 5

(2) INFORMATION FOR SEQ ID NO:70:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:70:

Ser Ser Lys Lys Leu Ala Leu Cys Tyr
     1                 5

PEPTIDE INHIBITORS OF SELECTIN BINDING

This application is filed under 35 USC 371 of PCT/US93/12110, filed 13 Dec. 1993, which is a CIP of U.S. application Ser. No. 07/997,771, filed 18 Dec. 1992, now abandoned.

BACKGROUND OF THE INVENTION

This invention relates to peptides which inhibit binding of selectins such as P-selectin, E-selectin and L-selectin.

The adherence of platelets and leukocytes to vascular surfaces is a critical component of the inflammatory response and is part of a complex series of reactions involving the simultaneous and interrelated activation of the complement, coagulation, and immune systems.

The complement proteins collectively play a leading role in the immune system, both in the identification and in the removal of foreign substances and immune complexes, as reviewed by Muller-Eberhard, H. J., *Ann. Rev. Biochem.* 57: 321–347 (1988). Central to the complement system are the C3 and C4 proteins, which when activated covalently attach to nearby targets, marking them for clearance. In order to help control this process, a remarkable family of soluble and membrane-bound regulatory proteins has evolved, each of which interacts with activated C3 and/or C4 derivatives. The coagulation and inflammatory pathways are regulated in a coordinate fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes.

Leukocyte adherence to vascular endothelium is a key initial step in migration of leukocytes to tissues in response to microbial invasion. Although a class of inducible leukocyte receptors, the CD11–CD18 molecules, are thought to have some role in adherence to endothelium, mechanisms of equal or even greater importance for leukocyte adherence appear to be due to inducible changes in the endothelium itself.

Activated platelets have also been shown to interact with both neutrophils and monocytes in vitro. The interaction of platelets with monocytes may be mediated in part by the binding of thrombospondin to platelets and monocytes, although other mechanisms have not been excluded. The mechanisms for the binding of neutrophils to activated platelets are not well understood, except that it is known that divalent cations are required. In response to vascular injury, platelets are known to adhere to subendothelial surfaces, become activated, and support coagulation. Platelets and other cells may also play an important role in the recruitment of leukocytes into the wound in order to contain microbial invasion.

Endothelium exposed to "rapid" activators such as thrombin and histamine becomes adhesive for neutrophils within two to ten minutes, while endothelium exposed to cytokines such as tumor necrosis factor and interleukin-1 becomes adhesive after one to six hours. The rapid endothelial-dependent leukocyte adhesion has been associated with expression of the lipid mediator platelet activating factor (PAF) on the cell surface, and presumably, the appearance of other endothelial surface receptors. The slower cytokine-inducible endothelial adhesion for leukocytes is mediated, at least in part, by E-selectin that is synthesized by endothelial cells after exposure to cytokines and then transported to the cell surface, where it binds neutrophils. The isolation, characterization and cloning of E-selectin or ELAM-1 is reviewed by Bevilacqua, et al., in *Science* 243, 1160–1165 (1989). L-selectin, a peripheral lymph node homing receptor, also called "the murine Mel 14 antigen", "Leu 8", the "Leu 8 antigen" and "LAM-1", is another structure on neutrophils, monocytes, and lymphocytes that binds lymphocytes to high endothelial venules in peripheral lymph nodes. The characterization and cloning of the protein is reviewed by Lasky, et al., *Cell* 56, 1045–1055 (1989) (mouse) and Tedder, et al., *J. Exp. Med.* 170, 123–133 (1989).

P-selectin, also known as GMP-140 (granule membrane protein 140), or PADGEM, is a cysteine-rich and heavily glycosylated integral membrane glycoprotein with an apparent molecular weight of 140,000 as assessed by sodium dodecyl sulfate polyacrylamide gel electrophoresis (SDS-PAGE). P-selectin was first purified from human platelets by McEver and Martin, *J. Biol. Chem.* 259: 9799–9804 (1984). The protein is present in alpha granules of resting platelets but is rapidly redistributed to the plasma membrane following platelet activation, as reported by Stenberg, et al., (1985). The presence of P-selectin in endothelial cells and its biosynthesis by these cells was reported by McEver, et al., *Blood* 70(5) Suppl. 1:355a, Abstract No. 1274 (1987). In endothelial cells, P-selectin is found in storage granules known as the Weibel-Palade bodies. (McEver, et al. *J. Clin. Invest.* 84: 92–99 (1989) and Hattori, et al., *J. Biol. Chem.* 264: 7768–7771 (1989)). P-selectin (called GMP-140 or PADGEM) has also been reported to mediate the interaction of activated platelets with neutrophils and monocytes by Larsen, et al., in *Cell* 59, 305–312 (October 1989) and Hamburger and McEver, *Blood* 75: 550–554 (1990).

The cDNA-derived amino acid sequence, reported by Johnston, et al., in *Cell* 56, 1033–1044 (Mar. 24 1989), and in U.S. Ser. No. 07/320,408 filed Mar. 8, 1989, now U.S. Pat. No. 5,378,464, indicates that it contains a number of modular domains that are likely to fold independently. Beginning at the N-terminus, these include a "lectin" domain, an "EGF" domain, nine tandem consensus repeats similar to those in complement binding proteins, a transmembrane domain (except in a soluble form that appears to result from differential splicing), and a cytoplasmic tail.

When platelets or endothelial cells are activated by mediators such as thrombin, the membranes of the storage granules fuse with the plasma membrane, the soluble contents of the granules are released to the external environment, and membrane bound P-selectin is presented within seconds on the cell surface. The rapid redistribution of P-selectin to the surface of platelets and endothelial cells as a result of activation suggested that this glycoprotein could play an important role at sites of inflammation or vascular disruption.

This important role has been confirmed by the observation that P-selectin is a receptor for neutrophils (Geng et al., *Nature* 343:757–760 (1990); Hamburger and McEver, *Blood* 75:550–554 (1990)), monocytes (Larsen, et al. *Cell* 59:305–312 (1989)); Moore, et al., *J. Cell Biol.* 112:491–499 (1991)), and perhaps a subset of lymphocytes (Moore, et al. *J. Cell Biol.* 112:491–499 (1991)). Thus, GMP-140 can serve as a receptor for leukocytes following its rapid mobilization to the surfaces of platelets and endothelia cells stimulated with agonists such as thrombin. This role in leukocyte recruitment may be important in hemostatic and inflammatory processes in both physiologic and pathologic states.

Peptides derived from P-selectin are described in U.S. Ser. No. 07/554,199 now abandoned, entitled "Functionally Active Selectin-Derived Peptides" filed Jul. 17, 1990 by Rodger P. McEver that are useful in diagnostics and in modulating the hemostatic and inflammatory responses in a patient wherein a therapeutically effective amount of a peptide capable of blocking leukocyte recognition of P-selectin is administered to the patient. U.S. Ser. No. 07/554,199 filed Jul. 17, 1990, now abandoned, also discloses that peptide sequences within the lectin domain of P-selectin, having homology with the lectin domains of other proteins, especially E-selectin and the L-selectin, selectively inhibit neutrophil adhesion to purified P-selectin, and can therefore be used in diagnostic assays of patients and diseases characterized by altered binding by these molecules, in screening assays for compounds altering this binding, and in clinical applications to inhibit or modulate interactions of leukocytes with platelets or endothelial cells involving coagulation and/or inflammatory processes.

E-selectin, L-selectin, and P-selectin have been termed "selectins", based on their related structure and function. E-selectin is not present in unstimulated endothelium. However, when endothelium is exposed to cytokines such as tumor necrosis factor of interleukin-1, the gene for E-selectin is transcribed, producing RNA which in turn is translated into protein. The result is that E-selectin is expressed on the surface of endothelial cells one to four hours after exposure to cytokines, as reported by Bevilacqua et al., *Proc.Natl.Acad. Sci.USA* 84: 9238–9242 (1987) (in contrast to P-selectin, which is stored in granules and presented on the cell surface within seconds after activation). E-selectin has been shown to mediate the adherence of neutrophils to cytokine-treated endothelium and thus appears to be important in allowing leukocytes to migrate across cytokine-stimulated endothelium into tissues. The cDNA-derived primary structure of E-selectin indicates that it contains a "lectin" domain, an EGF domain, and six (instead of the nine in P-selectin) repeats similar to those of complement-regulatory proteins, a transmembrane domain, and a short cytoplasmic tail. There is extensive sequence homology between P-selectin and E-selectin throughout both proteins, but the similarity is particularly striking in the lectin and EGF domains.

Homing receptors are lymphocyte surface structures that allow lymphocytes to bind to specialized endothelial cells in lymphatic tissues, termed high endothelial cells or high endothelial venules (reviewed by Yednock and Rosen, *Advances in Immunology*, vol. 44, F. I. Dixon, ed., 313–378 (Academic Press, New York 1989). This binding allows lymphocytes to migrate across the endothelium into the lymphatic tissues where they are exposed to processed antigens. The lymphocytes then re-enter the blood through the lymphatic system. L-selectin, a lymphocyte homing receptor, contains a lectin domain, an EGF domain, two complement-binding repeats, a transmembrane domain, and a short cytoplasmic tail. L-selectin also shares extensive sequence homology with P-selectin, particularly in the lectin and EGF domains.

Based on a comparison of the lectin domains between P-selectin, E-selectin, and L-selectin, it may be possible to select those peptides inhibiting binding of neutrophils to P-selectin which will inhibit binding of E-selectin, L-selectin, and other homologous selectins, to components of the inflammatory process, or, conversely, which will inhibit only P-selectin binding.

The in vivo significance of platelet-leukocyte interactions has not been studied carefully. However, in response to vascular injury, platelets are known to adhere to subendothelial surfaces, become activated, and support coagulation. Platelets and other cells may also play an important role in the recruitment of leukocytes into the wound in order to contain microbial invasion. Conversely, leukocytes may recruit platelets into tissues at sites of inflammation, as reported by Issekutz, et al., *Lab. Invest.* 49:716 (1983).

The coagulation and inflammatory pathways are regulated in a coordinate fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes.

Proteins involved in the hemostatic and inflammatory pathways are of interest for diagnostic purposes and treatment of human disorders. However, there are many problems using proteins therapeutically. Proteins are usually expensive to produce in quantities sufficient for administration to a patient. Moreover, there can be a reaction against the protein after it has been administered more than once to the patient. It is therefore desirable to develop peptides having the same, or better, activity as the protein, which are inexpensive to synthesize, reproducible and relatively innocuous.

It is preferable to develop peptides which can be prepared synthetically, having activity at least equal to, or greater than, the peptides derived from the protein itself.

It is therefore an object of the present invention to provide peptides interacting with cells recognized by selectins, including P-selectin, E-selectin, and L-selectin.

It is another object of the present invention to provide methods for using these peptides to inhibit leukocyte adhesion to endothelium or to platelets.

It is a further object of the present invention to provide methods for using these peptides to modulate the immune response and the hemostatic pathway.

It is yet another object of the present invention to provide peptides for use in diagnostic assays relating to P-selectin, E-selectin and L-selectin.

SUMMARY OF THE INVENTION

This invention relates to novel peptides having as their core region portions of the 109–118 amino acid sequence of P-selectin, E-selectin or L-selectin. More specifically, this invention relates to novel peptides of Formulas I and II:

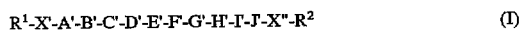

or pharmaceutically acceptable salts thereof, wherein:

X' is an N-terminus amino acid linear sequence of from zero to 10 amino acids, and $R^1$ is a moiety attached to the terminal α amino group of X', or the terminal α-amino group of the adjacent amino acid if X is zero;

X" is a C-terminus amino acid linear sequence of from zero to 10 amino acids, and $R^2$ is a moiety attached to the carboxyl carbon of X" or the carboxyl carbon of the adjacent amino acid if X" is zero;

A' is null (signifying no amino acid) or D- or L-cysteine;
A" is D- or L-cysteine;
B' is D- or L-histidine, D- or L-serine, D- or L-leucine, D- or L-phenylalanine, D- or L-asparagine, D- or L-proline or D- or L-glutamine;

C' is D- or L-lysine, D- or L-histidine, D- or L-arginine, or D- or L-serine;

D' is D- or L-lysine, D- or L-leucine, D- or L-alanine, D- or L-phenylalanine, D- or L-histidine, D- or L-arginine, or D- or L-serine;

E' is D- or L-lysine, D- or L-phenylalanine, D- or L-glutamine, or D- or L-arginine;

F' is D- or L-histidine, D- or L-leucine, D- or L-alanine, D- or L-isoleucine, D- or L-threonine, or D- or L-arginine;

G' is D- or L-alanine, D- or L-phenylalanine, D- or L-histidine, D- or L-isoleucine, or D- or L-glutamine;

H' is D- or L-leucine, D- or L-phenylalanine, D- or L-isoleucine, D- or L-proline, or D- or L-alanine;

I' is D- or L-cysteine, D- or L-phenylalanine, D- or L-isoleucine, D- or L-histidine, D- or L-leucine, D- or L-valine, D- or L-threonine, or D- or L-serine;

I" is D- or L-cysteine;

J' is D- or L-tyrosine, D- or L-phenylalanine, D- or L-isoleucine, or D- or L-valine;

$R^1$ is hydrogen (signifying a free N-terminal group), lower alkyl, aryl, formyl, alkanoyl, aroyl, alkyloxycarbonyl or aryloxycarbonyl;

$R^2$ is OH (signifying a free C-terminal carboxylic acid), $OR^3$, signifying ester, where $R^3$ is lower alkyl or aryl or $R^2$ is $NR^5R^6$ where $R^5$ and $R^6$ are each selected independently from hydrogen, lower alkyl, aryl or cyclic alkyl.

The peptides of Formulas I and II have as their core region the 109–118 amino acid sequence of the selectins. Residue 1 is defined as the N-terminus of the mature protein after the cleavage of the signal peptide.

The peptides of Formulas I and II should inhibit the binding of neutrophils to P-selectin in concentrations of peptide ranging from about 10 to about 1500 μM. Tests also indicate that alterations within the core sequence, as well as N-terminal and C-terminal flanking regions, do not result in loss of biological activity.

This invention relates not only to the novel peptides of Formulas I and II, but also to pharmaceutical compositions comprising them, to diagnostic and therapeutic methods utilizing them, and to methods of preparing them.

DETAILED DESCRIPTION OF THE INVENTION

Preferred peptides of this invention are those of Formula I and II wherein, together or independently: $R^1$ is hydrogen or acetyl (Ac) and $R^2$ is OH or $NH_2$. More preferred are those peptides wherein $R^2$ is $NH_2$.

One group of preferred peptides includes those of Formula I where, independently, A' is null, B' is Phe, His, Leu, Asn or Ser; C' is Lys or Arg; D' is Lys, Phe, Leu, Ala; E' is Lys or Arg; F' is Leu or Arg; G' is Ala; H' is Leu; I' is Cys, Ile or Phe, and J' is Tyr.

Test results have indicated that peptides in which E' is Arg have superior activity. Accordingly, a more preferred group of peptides are those in which E' is Arg.

Specifically preferred peptides include the following:

(SEQ ID NO:1) Cys—Leu—Lys—Lys—Lys—His—Ala—Leu—Cys—Tyr—NH$_2$;

(SEQ ID NO:2) Cys—Ser—Lys—Lys—Lys—Leu—Ala—Leu—Cys—Tyr—NH$_2$;

(SEQ ID NO:3) Cys—His—Lys—Leu—Lys—Ala—Ala—Leu—Cys—Tyr—NH$_2$;

(SEQ ID NO:4) cyclo-(Cys—Leu—Lys—Lys—Lys—His—Ala—Leu—Cys)—Tyr—NH$_2$;

(SEQ ID NO:5) cyclo-(Cys—Ser—Lys—Lys—Lys—Leu—Ala—Leu—Cys)—Tyr—NH$_2$;

(SEQ ID NO:6) cyclo-(Cys—His—Lys—Leu—Lys—Ala—Ala—Leu—Cys)—Tyr—NH$_2$;

(SEQ ID NO:7) Ac—Phe—Lys—Lys—Lys—Leu—Ala—Leu—Cys—Tyr—NH$_2$;

(SEQ ID NO:8) Phe—Lys—Lys—Lys—Leu—Ala—Leu—Cys—Tyr—NH$_2$;

(SEQ ID NO:9) Ac—His—Lys—Lys—Lys—Leu—Ala—Leu—Cys—Tyr—NH$_2$;

(SEQ ID NO:10) His—Lys—Lys—Lys—Leu—Ala—Leu—Cys—Tyr—NH$_2$;

(SEQ ID NO:11) Leu—Lys—Lys—Lys—His—Ala—Leu—Cys—Tyr—NH$_2$;

(SEQ ID NO:12) Ac—Leu—Lys—Lys—Lys—Leu—Ala—Leu—Cys—Tyr—NH$_2$;

(SEQ ID NO:13) Leu—Lys—Lys—Lys—Leu—Ala—Leu—Cys—Tyr—NH$_2$;

(SEQ ID NO:14) Ac—Asn—Lys—Lys—Lys—Leu—Ala—Leu—Cys—Tyr—NH$_2$;

(SEQ ID NO:15) Asn—Lys—Lys—Lys—Leu—Ala—Leu—Cys—Tyr—NH$_2$;

(SEQ ID NO:16) Pro—Lys—Lys—Lys—Leu—Ala—Leu—Cys—Tyr—NH$_2$;

(SEQ ID NO:17) Gln—Lys—Lys—Lys—Leu—Ala—Leu—Cys—Tyr—NH$_2$;

(SEQ ID NO:18) Ser—His—Lys—Lys—Leu—Ala—Leu—Cys—Tyr—NH$_2$;

(SEQ ID NO:19) Ac—Ser—Lys—Ala—Lys—Leu—Ala—Leu—Cys—Tyr—NH$_2$;

(SEQ ID NO:20) Ser—Lys—Phe—Lys—Leu—Ala—Leu—Cys—Tyr—NH$_2$;

(SEQ ID NO:21) Ser—Lys—His—Lys—Leu—Ala—Leu—Cys—Tyr—NH$_2$;

(SEQ ID NO:22) Ser—Lys—Lys—Phe—Leu—Ala—Leu—Cys—Tyr—NH$_2$;

(SEQ ID NO:23) Ac—Ser—Lys—Lys—Lys—Ala—Ala—Leu—Cys—Tyr—NH$_2$;

-continued (SEQ ID NO:24) Ser—Lys—Lys—Lys—Ala—Ala—Leu—Cys—Tyr—NH$_2$;

(SEQ ID NO:25) Ser—Lys—Lys—Lys—His—Ala—Leu—Cys—Tyr—NH$_2$;

(SEQ ID NO:26) Ser—Lys—Lys—Lys—Ile—Ala—Leu—Cys—Tyr—NH$_2$;

(SEQ ID NO:27) Ser—Lys—Lys—Lys—Leu—Ala—Phe—Cys—Tyr—NH$_2$;

(SEQ ID NO:28) Ser—Lys—Lys—Lys—Leu—Ala—Ile—Cys—Tyr—NH$_2$;

(SEQ ID NO:29) Ser—Lys—Lys—Lys—Leu—Ala—Leu—Cys—Phe—NH$_2$;

(SEQ ID NO:30) Ser—Lys—Lys—Lys—Leu—Ala—Leu—Cys—Ile—NH$_2$;

(SEQ ID NO:31) Ser—Lys—Lys—Lys—Leu—Ala—Leu—Cys—Tyr—NH$_2$;

(SEQ ID NO:32) Ser—Lys—Lys—Lys—Leu—Ala—Leu—Phe—Tyr—NH$_2$;

(SEQ ID NO:33) Ser—Lys—Lys—Lys—Leu—Ala—Leu—Ile—Val—NH$_2$;

(SEQ ID NO:34) Ac—Ser—Lys—Lys—Lys—Leu—Ala—Leu—Ile—Tyr—NH$_2$;

(SEQ ID NO:35) Ser—Lys—Lys—Lys—Leu—Ala—Leu—Ile—Tyr—NH$_2$;

(SEQ ID NO:36) Ser—Lys—Lys—Lys—Leu—Ala—Leu—His—Tyr—NH$_2$;

(SEQ ID NO:37) Ac—Ser—Lys—Lys—Lys—Leu—Ala—Leu—Leu—Tyr—NH$_2$;

(SEQ ID NO:38) Ser—Lys—Lys—Lys—Leu—Ala—Leu—Leu—Tyr—NH$_2$;

(SEQ ID NO:39) Ac—Ser—Lys—Lys—Lys—Leu—Ala—Leu—Val—Tyr—NH$_2$;

(SEQ ID NO:40) Ser—Lys—Lys—Lys—Leu—Ala—Leu—Val—Tyr—NH$_2$;

(SEQ ID NO:41) Ser—Lys—Lys—Lys—Leu—Ala—Leu—Thr—Tyr—NH$_2$;

(SEQ ID NO:42) Ser—Lys—Lys—Lys—Leu—Ala—Pro—Cys—Tyr—NH$_2$;

(SEQ ID NO:43) Ser—Lys—Lys—Lys—Leu—Phe—Leu—Cys—Tyr—NH$_2$;

(SEQ ID NO:44) Ser—Lys—Lys—Lys—Leu—His—Leu—Cys—Tyr—NH$_2$;

(SEQ ID NO:45) Ser—Lys—Lys—Lys—Leu—Ile—Leu—Cys—Tyr—NH$_2$;

(SEQ ID NO:46) Ser—Lys—Lys—Lys—Leu—Gln—Ala—Cys—Tyr—NH$_2$;

(SEQ ID NO:47) Ac—Ser—Lys—Lys—Lys—Thr—Ala—Leu—Cys—Tyr—NH$_2$;

(SEQ ID NO:48) Ser—Lys—Lys—Gln—Leu—Ala—Leu—Cys—Tyr—NH$_2$;

(SEQ ID NO:49) Ac—Ser—Lys—Lys—Arg—Leu—Ala—Leu—Cys—Tyr—NH$_2$;

(SEQ ID NO:50) Ser—Lys—Lys—Arg—Leu—Ala—Leu—Cys—Tyr—NH$_2$;

(SEQ ID NO:51) Ac—Ser—Lys—Leu—Lys—Leu—Ala—Leu—Cys—Tyr—NH$_2$;

(SEQ ID NO:52) Ser—Lys—Leu—Lys—Leu—Ala—Leu—Cys—Tyr—NH$_2$;

(SEQ ID NO:53) Ac—Ser—Lys—Arg—Lys—Leu—Ala—Leu—Cys—Tyr—NH$_2$;

(SEQ ID NO:54) Ser—Lys—Arg—Lys—Leu—Ala—Leu—Cys—Tyr—NH$_2$;

(SEQ ID NO:55) Ac—Ser—Lys—Arg—Lys—Arg—Ala—Leu—Cys—Tyr—NH$_2$;

(SEQ ID NO:56) Ser—Lys—Arg—Lys—Arg—Ala—Leu—Cys—Tyr—NH$_2$;

(SEQ ID NO:57) Ac—Ser—Lys—Arg—Arg—Leu—Ala—Leu—Cys—Tyr—NH$_2$;

(SEQ ID NO:58) Ser—Lys—Arg—Arg—Leu—Ala—Leu—Cys—Tyr—NH$_2$;

(SEQ ID NO:59) Ser—Lys—Arg—Arg—Leu—Ala—Leu—Ser—Tyr—NH$_2$;

(SEQ ID NO:60) Ser—Lys—Ser—Lys—Leu—Ala—Leu—Cys—Tyr—NH$_2$;

(SEQ ID NO:61) Ac—Ser—Arg—Ala—Arg—Leu—Ala—Leu—Cys—Tyr—NH$_2$;

(SEQ ID NO:62) Ser—Arg—Ala—Arg—Leu—Ala—Leu—Cys—Tyr—NH$_2$;

(SEQ ID NO:63) Ac—Ser—Arg—Lys—Lys—Leu—Ala—Leu—Cys—Tyr—NH$_2$;

(SEQ ID NO:64) Ser—Arg—Lys—Lys—Leu—Ala—Leu—Cys—Tyr—NH₂;

(SEQ ID NO:65) Ac—Ser—Arg—Lys—Arg—Leu—Ala—Leu—Cys—Tyr—NH₂;

(SEQ ID NO:66) Ser—Arg—Lys—Arg—Leu—Ala—Leu—Cys—Tyr—NH₂;

(SEQ ID NO:67) Ser—Arg—Lys—Arg—Leu—Ala—Leu—Ser—Tyr—NH₂;

(SEQ ID NO:68) Ac—Ser—Arg—Arg—Lys—Leu—Ala—Leu—Cys—Tyr—NH₂;

(SEQ ID NO:69) Ser—Arg—Arg—Lys—Leu—Ala—Leu—Cys—Tyr—NH₂;

(SEQ ID NO:70) Ser—Ser—Lys—Lys—Leu—Ala—Leu—Cys—Tyr—NH₂;

More preferred peptides are those with Sequence ID Nos. 2, 6, 8, 9, 12, 15, 20, 31, 33, 35, 49, 50, 51, 52, 53, 54, 55, 56, 57, 58, 61, 62, 63, 64, 65, 66, 68, and 69.

As used herein, the term "alkyl" includes branched, straight-chain, and cyclic saturated hydrocarbons. The term "lower alkyl" means an alkyl having from one to six carbon atoms, such as methyl, ethyl, propyl, isopropyl, butyl, isobutyl, t-butyl, pentyl, isopentyl, neopentyl, cyclopentylmethyl and hexyl. The term "alkanoyl" means

wherein R⁷ is a alkyl group.
The term "aroyl" means

wherein R⁸ is an aryl group. The term "aryl" means an aromatic or heteroaromatic structure having between one and three rings, which may or may not be ring fused structures, and are optionally substituted with halogens, carbons, or other heteroatoms such as nitrogen (N), sulfur (S), phosphorus (P), and boron (B).
The term alkoxycarbonyl means

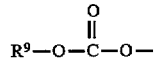

wherein R⁹ is a lower alkyl group.
The term aryloxycarbonyl means

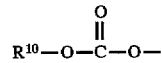

wherein R¹⁰ is an aryl and arylmethyl group.

Halogen refers to fluorine, chlorine, bromine or iodine.

The term "terminal α-amino group of X" refers to the α-amino group of the N-terminal amino acid of X.

The peptides of Formulas I and II can be used in the form of the free peptide or a pharmaceutically acceptable salt. Amine salts can be prepared by treating the peptide with an acid according to known methods. Suitable acids include inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid, and sulfanilic acid.

Carboxylic acid groups in the peptide can be converted to a salt by treating the peptide with a base according to known methods. Suitable bases include inorganic bases such as sodium hydroxide, ammonium hydroxide, and potassium hydroxide, and organic bases such as mono-, di-, and tri-alkyl and aryl amines (e.g., triethylamine, diisopropylamine, methylamine, and dimethylamine and optionally substituted mono-, di, and tri-ethanolamines).

As referred to herein, the amino acid components of the peptides and certain materials used in their preparation are identified by abbreviations for convenience. These abbreviations are as follows:

| Amino Acid | Abbreviations | |
|---|---|---|
| L-alanine | Ala | A |
| D-alanine | D-Ala | a |
| L-arginine | Arg | R |
| D-arginine | D-Arg | r |
| D-asparagine | D-Asn | n |
| L-asparagine | Asn | N |
| L-aspartic acid | Asp | D |
| D-aspartic acid | D-Asp | d |
| L-cysteine | Cys | C |
| D-cysteine | D-Cys | c |
| L-glutamic acid | Glu | E |
| D-glutamic acid | D-Glu | e |
| L-glutamine | Gln | Q |
| D-glutamine | D-Gln | q |
| glycine | Gly | G |
| L-histidine | His | H |
| D-histidine | D-His | h |
| L-isoleucine | Ile | I |
| D-isoleucine | D-Ile | i |
| L-leucine | Leu | L |
| D-leucine | D-Leu | l |
| L-lysine | Lys | K |
| D-lysine | D-Lys | k |
| L-phenylalanine | Phe | F |
| D-phenylalanine | D-Phe | f |
| L-proline | Pro | P |
| D-proline | D-Pro | p |
| L-serine | Ser | S |
| D-serine | D-Ser | s |
| L-threonine | Thr | T |
| D-threonine | D-Thr | t |
| L-tyrosine | Tyr | Y |
| D-tyrosine | D-Tyr | y |
| L-tryptophan | Trp | W |
| D-tryptophan | D-Trp | w |
| L-valine | Val | V |
| D-valine | D-Val | v |
| L-methionine | Met | M |
| D-methionine | D-Met | m |
| Reagents | | |
| Trifluoroacetic acid | TFA | |
| Methylene chloride | CH₂Cl₂ | |
| N,N-Diisopropylethylamine | DIEA | |
| N-Methylpyrrolidone | NMP | |
| 1-Hydroxybenzotriazole | HOBT | |
| Dimethylsulfoxide | DMSO | |

| | Abbreviations |
|---|---|
| Acetic anhydride | Ac$_2$O |
| Diisopropylcarbodiimide | DIC |
| Acetic acid | HOAc |

Amino acids preceded by L- or D- refer, respectively, to the L- or D- enantiomer of the amino acid, whereas amino acids not preceded by L- or D- refer to the L-enantiomer.

Methods of Preparation of Peptides

The peptides can generally be prepared following known techniques, as described, for example, in the cited publications, the teachings of which are specifically incorporated herein. In a preferred method, the peptides are prepared following the solid-phase synthetic technique initially described by Merrifield in *J.Amer.Chem.Soc.*, 85, 2149–2154 (1963). Other techniques may be found, for example, in M. Bodanszky, et al, *Peptide Synthesis*, second edition, (John Wiley & Sons, 1976), as well as in other reference works known to those skilled in the art.

Appropriate protective groups usable in such syntheses and their abbreviations will be found in the above text, as well as in J. F. W. McOmie, *Protective Groups in Organic Chemistry*, (Plenum Press, New York, 1973). The common protective groups used herein are t-butyloxycarbonyl (Boc), fluorenylmethoxycarboyl (FMOC), benzyl (Bzl), tosyl (Tos), o-bromo-phenylmethoxycarbonyl (BrCBZ), phenylmethoxycarbonyl (CBZ), 2-chloro-phenylmethoxycarbonyl (2-Cl-CBZ), 4-methoxy-2,3,6-trimethylbenzenesulfonyl (Mtr), trityl (rrt), formyl (CHO), and tertiary butyl (t-Bu).

General synthetic procedures for the synthesis of peptides of Formula I and II the invention by solid phase methodology are as follows:

A. General Synthetic Procedures For Solid Phase Peptide Synthesis Using N$^\alpha$-Boc Protection

| | REPETITIONS | TIME |
|---|---|---|
| 1. 25% TFA in CH$_2$Cl$_2$ | 1 | 3 min. |
| 2. 50% TFA in CH$_2$Cl$_2$ | 1 | 16 min. |
| 3. CH$_2$Cl$_2$ | 5 | 3 min. |
| 4. 5% DIEA in NMP | 2 | 4 min. |
| 5. NMP | 6 | 5 min. |
| 6. Coupling step | 1 | 57 min. |
| a. Preformed BOC-Amino Acid-HOBT active ester in NMP | | 37 min. |
| b. DMSO | | 16 min. |
| c. DIEA | | 5 min. |
| 7. 10% Ac$_2$O, 5% DIEA in NMP | 1 | 9 min. |
| 8. CH$_2$Cl$_2$ | 5 | 3 min. |

B. General Synthetic Procedure For Solid Phase Peptide Synthesis Using N$^\alpha$-FMOC Protection

| | REPETITIONS | TIME |
|---|---|---|
| 1. 50% piperidine in DMF | 1 | 1 min. |
| 2. 50% piperidine in NMP | 1 | 12 min. |
| 3. NMP | 7 | 1 min. |
| 4. Coupling | 1 | 71 min. |
| Amino acid and HOBT in NMP added to the resin followed by the addition of DIC in NMP. | | |
| HOBT active ester in NMP or | | |
| 5. NMP | 1 | 1 min. |
| 6. Repeat steps 4–5 | 1 | |
| 7. NMP | 2 | 1 min. |

N-terminal acetylation on the deprotected N$^\alpha$-amino group of peptides synthesized using either Boc or FMOC strategies can be accomplished with 10% Ac$_2$O and 5% DIEA in NMP, followed by washing of the peptide resin with NMP and/or CH$_2$Cl$_2$.

The peptides can also be prepared using standard genetic engineering techniques known to those skilled in the art. For example, the peptide can be produced enzymatically by inserting nucleic acid encoding the peptide into an expression vector, expressing the DNA, and translating the DNA into the peptide in the presence of the required amino acids. The peptide is then purified using chromatographic or electrophoretic techniques, or by means of a carrier protein which can be fused to, and subsequently cleaved from, the peptide by inserting into the expression vector in phase with the peptide encoding sequence a nucleic acid sequence encoding the carrier protein. The fusion protein-peptide may be isolated using chromatographic, electrophoretic or immunological techniques (such as binding to a resin via an antibody to the carrier protein). The peptide can be cleaved using chemical methodology or enzymatically, as by, for example, hydrolases.

Peptides of the invention can also be prepared using solution methods, by either stepwise or fragment condensations. An appropriately alpha amino-protected amino acid is coupled to an appropriately alpha carboxyl protected amino acid (such protection may not be required depending on the coupling method chosen) using diimides, symmetrical or unsymmetrical anhydrides, BOP, or other coupling reagents or techniques known to those skilled in the art. These techniques may be either or enzymatic. The alpha amino and/or alpha carboxyl protecting groups are removed and the next suitably protected amino acid or block of amino acids are coupled to extend the growing peptide. Various combinations of protecting groups and of chemical and/or enzymatic techniques and assembly strategies can be used in each synthesis.

The peptides of Formula II are cyclic by virtue of the formation of a disulfide bond between cysteine residues. The general techniques for the formation of this bond are described by G. Barany and R. B. Merrifield in *The Peptides Analysis, Synthesis, Biology*, (Academic Press, Inc., 1979), as well as in other reference works known to those skilled in the art.

Methods of Preparation of Pharmaceutical Compositions

Pharmaceutical compositions of this invention comprise a pharmaceutically acceptable carrier or diluent and an effective quantity of one or more of the peptides of Formula I or II or an acid or base salt thereof. The carrier or diluent may take a wide variety of forms depending on the form of preparation desired for administration, e.g., sublingual, rectal, nasal, oral, or parenteral.

In preparing the compositions in oral dosage form, any of the usual pharmaceutical media may be employed, for example, waters, oils, alcohols, flavoring agents, preservatives, and coloring agents, to make an oral liquid preparation (e.g., suspension, elixir, or solution) or with carriers such as starches, sugars, diluents, granulating agents, lubricants, binders, and disintegrating agents, to make an oral solid preparation (e.g., powder, capsule, or tablet).

Controlled release forms or enhancers to increase bioavailability may also be used. Because of their ease in administration, tablets and capsules represent the most advantageous oral dosage unit form, in which case solid pharmaceutical carriers are employed. If desired, tablets may be sugar coated or enteric coated by standard techniques.

For parenteral products, the carrier will usually be sterile water, although other ingredients to aid solubility or as preservatives may be included. Injectable suspensions may also be prepared, in which case appropriate liquid carriers and suspending agents can be employed.

The peptides can also be administered locally at a wound or inflammatory site by topical application of a solution or cream.

Alternatively, the peptide may be administered in liposomes or microspheres (or microparticles). Methods for preparing liposomes and microspheres for administration to a patient are known to those skilled in the art. U.S. Pat. No. 4,789,734 describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14, "Liposomes", *Drug Carriers in Biology and Medicine*, pp. 287-341 (Academic Press, 1979). Microspheres formed of polymers or proteins are well known to those skilled in the art, and can be tailored for passage through the gastrointestinal tract directly into the bloodstream. Alternatively, the peptide can be incorporated and the microspheres, or composite of microspheres, implanted for slow release over a period of time, ranging from days to months. See, for example, U.S. Pat. Nos. 4,906,474, 4,925,673 and 3,625,214.

The peptides are generally active when administered parenterally in amounts of at least about 1 µg/kg body weight. Effective doses by other routes of administration are generally those which result in similar blood level to i.v. doses of at least about 1 µg/Kg. For treatment to prevent organ injury in cases involving reperfusion, the peptides may be administered parenterally in amounts from about 0.01 to about 10 mg/kg body weight. Generally, the same range of dosage amounts may be used in treatment of other diseases or of conditions where inflammation is to be reduced. This dosage will be dependent, in part, on whether one or more peptides are administered. A synergistic effect may be seen with combinations of peptides from different, or overlapping, regions of the lectin domain, or in combination with peptides derived from the EGF domain of P-, E- or L-selectin. For treatment to prevent organ injury in cases involving reperfusion, the peptides may be administered parenterally in amounts from about 0.01 to about 10 mg/kg body weight. Generally, the same range of dosage amounts may be used in treatment of other diseases or of conditions where inflammation is to be reduced. This dosage will be dependent, in part, on whether one or more peptides are administered. A synergistic effect may be seen with combinations of peptides from different, or overlapping, regions of the lectin domain, or in combination with peptides derived form the EGF domain of p-selectin.

Methods for Demonstrating Binding

Peptides that are biologically active are those which inhibit binding of neutrophils, monocytes, subsets of lymphocytes or other cells to P-selectin, or which inhibit leukocyte adhesion to endothelium that is mediated by ELAM-1 and/or the homing receptor.

Peptides can be screened for their ability to inhibit adhesion to cells, for example, neutrophil adhesion to purified P-selectin immobilized on plastic wells, using the assay described by Geng, et al., *Nature* 343, 757-760 1990).

Human neutrophils are isolated from heparinized indole blood by density gradient centrifugation on Mono-Poly resolving media, Flow Laboratories. Neutrophil suspensions are greater than 98% pure and greater than 95% viable by trypan blue exclusion. For adhesion assays, neutrophils are suspended at a concentration of $2 \times 10^6$ cells/mL in Hanks' balanced salt solution containing 1.26 mM $Ca^{2+}$ and 0.81 mM $Mg^{2+}$ (HBSS, Gibco) with g mg/mL human serum albumin (HBSS/HSA). Adhesion assays are conducted in triplicate in 96-well microtiter plates, Corning, incubated at 4° C. overnight with 50 microliters of various protein solutions.

P-selectin is isolated from human platelet lysates by immunoaffinity chromatography on antibody S12-Sepharose™ and ion-exchange chromatography on a Mono-Q™ column (FLPC, Pharmacia Fine Chemicals), as follows.

Outdated human platelet packs (100 units) obtained from a blood bank and stored at 4° C. are pooled, adjusted to 5 mM EDTA at pH 7.5, centrifuged at 4,000 rpm for 30 minutes in 1 liter bottles, then washed three times with 1 liter of 0.1M NaCl, 20 mM Tris pH 7.5 (TBS), 5 mM EDTA, 5 mM benzamidine.

The pellets are then resuspended in a minimum amount of wash buffer and made 1 mM in DIFP, then frozen in 50 mL screwtop tubes at -80° C. The frozen platelets are thawed and resuspended in 50 mL TBS, 5 mM benzamidine, 5 mM EDTA pH 7.5, 100M leupeptin. The suspension is frozen and thawed two times in a dry ice-acetone bath using a 600 mL lyophilizing flask, then homogenized in a glass/teflon mortar and pestle and made 1 mM in DIFP. The NaCl concentration is adjusted to 0.5M with a stock solution of 4M NaCl. After stirring the suspension at 4° C., it is centrifuged in polycarbonate tubes at 33,000 rpm for 60 minutes at 4° C. The supernatant (0.5M NaCl wash) is removed and saved; this supernatant contains the soluble form of P-selectin. Care is taken not to remove the top part of the pellet with the supernatant. The pellets are then homogenized in extraction buffer (TBS, 5 mM benzamidine, 5 mM EDTA, pH 7.5, 100 µM leupeptin, 2% Triton X-100). After centrifugation at 19,500 rpm for 25 minutes at 4° C., the supernatant is removed. The extraction procedure is repeated with the pellet and the supernatant is combined with the first supernatant. The combined extracts, which contain the membrane form of P-selectin, are adjusted to 0.5M NaCl.

The soluble fraction (0.5M NaCl wash) and the membrane extract (also adjusted to 0.5M NaCl) are absorbed with separate pools of the monoclonal antibody S12 (directed to P-selectin) previously coupled to Affigel (Biorad) at 5 mg/mL for 2 hours at 4° C. After letting the resins settle, the supernatants are removed. The S12 Affigel containing bound GMP-140 is then loaded into a column and washed overnight at 4° C. with 400 mL of 0.5M NaCl, 20 mM Tris pH 7.5, 0.01% Lubrol PX.

Bound P-selectin is eluted from the S12 Affigel with 100 mL of 80% ethylene glycol, 1 mM MES pH 6.0, 0.01% Lubrol PX. Peak fractions with absorbance at 280 nm are pooled. Eluates are dialyzed against TBS with 0.05% Lubrol, then applied to a Mono Q column (FPLC from Pharmacia). The concentrated protein is step eluted with 2M NaCl, 20 mM Tris pH 7.5 (plus 0.05% Lubrol PX for the membrane fraction). Peak fractions are dialyzed into TBS pH 7.5 (plus 0.05% Lubrol PX for the membrane fraction).

P-selectin is plated at 5 micrograms/mL and the control proteins: human serum albumin (Alb), platelet glycoprotein IIb/IIIa (IIb), von Willsbrand factor (vWF), fibrinogen (FIB), thrombomodulin (TM), gelatin (GEL) or human serum (HS), are added at 50 micrograms/mL. All wells are blocked for 2 hours at 22° C. with 300 microliters HBSS containing 10 mg/mL HSA, then washed three times with HBSS containing 0.1% Tween-20 and once with HBSS. Cells ($2\times10^5$ per well) are added to the wells and incubated at 22° C. for 20 minutes. The wells are then filled with HBSS/HSA, sealed with acetate tape (Dynatech), and centrifuged inverted at 150 g for 5 minutes. After discarding nonadherent cells and supernates, the contents of each well are solubilized with 200 microliters 0.5% hexadecyltrimethylammonium bromide, Sigma, in 50 mM potassium phosphate, pH. 6.0, and assayed for myeloperoxidase activity, Ley, et al., *Blood* 73, 1324–1330 (1989). The number of cells bound is derived from a standard curve of myeloperoxidase activity versus numbers of cells. Under all assay conditions, the cells release less than 5% of total myeloperoxidase and lactate dehydrogenase. Inhibition is read as a lower percent adhesion, so that a value of 5% means that 95% of the specific adhesion was inhibited.

Peptides are tested at concentrations between 1.0 mM to 0.001 mM and a percent inhibition calculated for each concentration. A least squares fit is done on a plot of peptide concentration versus percent inhibition and an $IC_{50}$ value calculated. The $IC_{50}$ is defined as the concentration of peptide that will inhibit 50% of the neutrophil binding to the P-selectin lawn.

Activity data are presented either as an $IC_{50}$ for each peptide or the percent inhibition at a defined concentration.

Table I gives the $IC_{50}$ values in mM for peptides of the invention in inhibiting the binding of human neutrophils to P-selectin.

TABLE I

INHIBITION OF BINDING OF HUMAN NEUTROPHILS TO P-SELECTIN

| Structure | | $IC_{50}$ (mM) |
|---|---|---|
| CLKKKHALCY—NH₂ | SEQ ID NO: 1 | 0.269 |
| CSKKKLALCY—NH₂ | SEQ ID NO: 2 | 0.048 |
| CHKLKAALCY—NH₂ | SEQ ID NO: 3 | 0.282 |
| Cyclo-(CLKKKHALC)—Y—NH₂ | SEQ ID NO: 4 | 0.626 |
| Cyclo-(CSKKKLALC)—Y—NH₂ | SEQ ID NO: 5 | 0.078 |
| Cyclo-(CHKLKAALC)—Y—NH₂ | SEQ ID NO: 6 | 0.002 |
| Ac-FKKKLALCY—NH₂ | SEQ ID NO: 7 | 0.074 |
| FKKKLALCY—NH₂ | SEQ ID NO: 8 | 0.020 |
| Ac-HKKKLALCY—NH₂ | SEQ ID NO: 9 | 0.011 |
| HKKKLALCY—NH₂ | SEQ ID NO: 10 | 0.055 |
| LKKKHALCY—NH₂ | SEQ ID NO: 11 | 0.178 |
| Ac-LKKKLALCY—NH₂ | SEQ ID NO: 12 | 0.026 |
| LKKKLALCY—NH₂ | SEQ ID NO: 13 | 0.065 |
| Ac-NKKKLALCY—NH₂ | SEQ ID NO: 14 | 0.053 |
| NKKKLALCY—NH₂ | SEQ ID NO: 15 | 0.019 |
| PKKKLALCY—NH₂ | SEQ ID NO: 16 | 0.103 |
| QKKKLALCY—NH₂ | SEQ ID NO: 17 | 1.013 |
| SHKKLALCY—NH₂ | SEQ ID NO: 18 | 0.362 |
| Ac-SKAKLALCY—NH₂ | SEQ ID NO: 19 | 0.060 |
| SKFKLALCY—NH₂ | SEQ ID NO: 20 | 0.037 |
| SKHKLALCY—NH₂ | SEQ ID NO: 21 | 0.888 |
| SKKFLALCY—NH₂ | SEQ ID NO: 22 | 0.554 |
| Ac-SKKKAALCY—NH₂ | SEQ ID NO: 23 | 0.192 |
| SKKKAALCY—NH₂ | SEQ ID NO: 24 | 0.232 |
| SKKKHALCY—NH₂ | SEQ ID NO: 25 | 0.656 |
| SKKKIALCY—NH₂ | SEQ ID NO: 26 | 0.062 |
| SKKKLAFCY—NH₂ | SEQ ID NO: 27 | 0.086 |
| SKKKLAICY—NH₂ | SEQ ID NO: 28 | 0.107 |
| SKKKLALCF—NH₂ | SEQ ID NO: 29 | 0.065 |
| SKKKLALCI—NH₂ | SEQ ID NO: 30 | 0.867 |
| SKKKLALCY—NH₂ | SEQ ID NO: 31 | 0.019 |
| SKKKLALFY—NH₂ | SEQ ID NO: 32 | 0.015 |

TABLE I-continued

INHIBITION OF BINDING OF HUMAN NEUTROPHILS TO P-SELECTIN

| Structure | | $IC_{50}$ (mM) |
|---|---|---|
| SKKKLALIV—NH₂ | SEQ ID NO: 33 | 0.390 |
| Ac-SKKKLALIY—NH₂ | SEQ ID NO: 34 | 0.128 |
| SKKKLALIY—NH₂ | SEQ ID NO: 35 | 0.043 |
| SKKKLALHY—NH₂ | SEQ ID NO: 36 | 0.177 |
| Ac-SKKKLALLY—NH₂ | SEQ ID NO: 37 | 0.088 |
| SKKKLALLY—NH₂ | SEQ ID NO: 38 | 0.131 |
| Ac-SKKKLALVY—NH₂ | SEQ ID NO: 39 | 0.164 |
| SKKKLALVY—NH₂ | SEQ ID NO: 40 | 0.233 |
| SKKKLALTY—NH₂ | SEQ ID NO: 41 | 0.423 |
| SKKKLAPCY—NH₂ | SEQ ID NO: 42 | 0.897 |
| SKKKLFLCY—NH₂ | SEQ ID NO: 43 | 0.095 |
| SKKKLHLCY—NH₂ | SEQ ID NO: 44 | 0.207 |
| SKKKLILCY—NH₂ | SEQ ID NO: 45 | 0.095 |
| SKKKLQACY—NH₂ | SEQ ID NO: 46 | 0.329 |
| Ac-SKKKTALCY—NH₂ | SEQ ID NO: 47 | 0.082 |
| SKKQLALCY—NH₂ | SEQ ID NO: 48 | 0.195 |
| Ac-SKKKLALCY—NH₂ | SEQ ID NO: 49 | 0.009 |
| SKKRLALCY—NH₂ | SEQ ID NO: 50 | 0.004 |
| Ac-SKLKLALCY—NH₂ | SEQ ID NO: 51 | 0.012 |
| SKLKLALCY—NH₂ | SEQ ID NO: 52 | 0.009 |
| Ac-SKRKLALCY—NH₂ | SEQ ID NO: 53 | 0.012 |
| SKRKLALCY—NH₂ | SEQ ID NO: 54 | 0.004 |
| Ac-SKRKRALCY—NH₂ | SEQ ID NO: 55 | 0.026 |
| SKRKRALCY—NH₂ | SEQ ID NO: 56 | 0.024 |
| Ac-SKRRLALCY—NH₂ | SEQ ID NO: 57 | 0.008 |
| SKRRLALCY—NH₂ | SEQ ID NO: 58 | 0.008 |
| SKRRLALSY—NH₂ | SEQ ID NO: 59 | 0.632 |
| SKSKLALCY—NH₂ | SEQ ID NO: 60 | 0.858 |
| Ac-SRARLALCY—NH₂ | SEQ ID NO: 61 | 0.047 |
| SRARLALCY—NH₂ | SEQ ID NO: 62 | 0.034 |
| Ac-SRKKLALCY—NH₂ | SEQ ID NO: 63 | 0.017 |
| SRKKLALCY—NH₂ | SEQ ID NO: 64 | 0.016 |
| Ac-SRKRLALCY—NH₂ | SEQ ID NO: 65 | 0.018 |
| SRKRLALCY—NH₂ | SEQ ID NO: 66 | 0.003 |
| SRKRLALSY—NH₂ | SEQ ID NO: 67 | 0.586 |
| Ac-SRRKLALCY—NH₂ | SEQ ID NO: 68 | 0.027 |
| SRRKLALCY—NH₂ | SEQ ID NO: 69 | 0.014 |
| SSKKLALCY—NH₂ | SEQ ID NO: 70 | 0.282 |

Clinical Applications

Since the selectins have several functions related to leukocyte adherence, inflammation, and coagulation, compounds which interfere with binding of P-selectin, E-selectin or L-selectin can be used to modulate these responses.

For example, the peptides can be used to competitively inhibit leukocyte adherence by competitively binding to P-selectin receptors on the surface of leukocytes. This kind of therapy would be particularly useful in acute situations where effective, but transient, inhibition of leukocyte-mediated inflammation is desirable. Chronic therapy by infusion of the peptides may also be feasible in some circumstances.

An inflammatory response may cause damage to the host if unchecked, because leukocytes release many toxic molecules that can damage normal tissues. These molecules include proteolytic enzymes and free radicals. Examples of pathological situations in which leukocytes can cause tissue damage include injury from ischemia and reperfusion, bacterial sepsis and disseminated intravascular coagulation, adult respiratory distress syndrome, tumor metastasis, rheumatoid arthritis and atherosclerosis.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., *Circulation* 67: 1016–1023 (1983)). These adherent leukocytes can migrate through the endothelium and destroy ischemic myocardium just as it is being rescued by restoration of blood flow.

There are a number of other common clinical disorders in which ischemia and reperfusion results in organ injury mediated by adherence of leukocytes to vascular surfaces, including strokes; mesenteric and peripheral vascular disease; organ transplantation; and circulatory shock (in this case many organs might be damaged following restoration of blood flow).

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system. Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products.

Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (lymphokine-activated lymphocytes). LAK cells are known to adhere to vascular walls and release products that are presumably toxic to endothelium. Although the mechanism by which LAK cells adhere to endothelium is now known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. The association of platelets with metastasizing tumor cells has been well described, suggesting a role for platelets in the spread of some cancers. Recently, it was reported that P-selectin binds to tumor cells in a variety of human carcinoma tissue sections (colon, lung, and breast), and that P-selectin binds to the cell surface of a number of cell lines derived from various carcinomas, but not from melanomas. Aruffo, A., et al., *Proc. Natl. Acad. Sci. USA*, 89, 2292–2296 (1992). Aruggo et al. also reference earlier work suggesting that E-selectin might be involved in tumor metastasis by mediating the adhesion of a colon carcinoma cell line (HT-20) to activated endothelial cells in vitro. Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia.

Another area of potential application is in the treatment of rheumatoid arthritis.

The criteria for assessing response to therapeutic modalities employing these peptides, and, hence, effective dosages of the peptides of this invention for treatment, are dictated by the specific condition and will generally follow standard medical practices. For example, the criteria for the effective dosage to prevent extension of myocardial infarction would be determined by one skilled in the art by looking at marker enzymes of myocardial necrosis in the plasma, by monitoring the electrocardiogram, vital signs, and clinical response. For treatment of acute respiratory distress syndrome, one would examine improvements in arterial oxygen, resolution of pulmonary infiltrates, and clinical improvement as measured by lessened dyspnea and tachypnea. For treatment of patients in shock (low blood pressure), the effective dosage would be based on the clinical response and specific measurements of function of vital organs such as the liver and kidney following restoration of blood pressure. Neurologic function would be monitored in patients with stroke. Specific tests are used to monitor the functioning of transplanted organs; for example, serum creatinine, urine flow, and serum electrolytes in patients undergoing kidney transplantation.

Diagnostic Reagents

The peptides can also be used for the detection of human disorders in which the ligands for the selectins might be defective. Such disorders would most likely be seen in patients with increased susceptibility to infections in which leukocytes might not be able to bind to activated platelets or endothelium. Cells to be tested, usually leukocytes, are collected by standard medically approved techniques and screened. Detection systems include ELISA procedures, binding of radiolabeled antibody to immobilized activated cells, flow cytometry, or other methods known to those skilled in the art. Inhibition of binding in the presence and absence of the lectin domain peptides can be used to detect defects or alterations in selectin binding. For selectins, such disorders would most likely be seen in patients with increased susceptibility to infections in which leukocytes would have defective binding to platelets and endothelium because of deficient leukocyte ligands for P-selectin.

The peptide is labeled radioactively, with a fluorescent tag, enzymatically, or with electron dense material such as gold for electron microscopy. The cells to be examined, usually leukocytes, are incubated with the labeled peptides and binding assessed by methods described above with antibodies to P-selectin, or by other methods known to those skilled in the art. If ligands for P-, E- or L-selectin are also found in the plasma, they can also be measured with standard ELISA or radioimmunoassay procedures, using labeled P-, E- or L-selectin-derived peptide instead of antibody as the detecting reagent.

The peptides can also be useful in in vivo imaging of concentrations of cells bearing selectin ligands. Cells expressing selectin ligands whose abnormally high local concentrations or presence within the body such as cancer cells, is indicative of a disorder can be imaged using labeled peptides. These labels may be either intrinsic or extrinsic to the structure of the specific selectin peptide and may include, but not be limited to high energy emitters such as $^{111}$In or non-radioactive dense atoms to enhance x-ray contrast.

The following examples are presented to illustrate, not limit, the invention. In the examples and throughout the specification, parts are by weight unless otherwise indicated.

EXAMPLE I

Cyclo-(cystinyl-leucyl-lysyl-lysyl-lysyl-histidyl-alanyl-leucyl-cystinyl)-tyrosine-amide (SEQ ID NO: 4)

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.84 g.

The peptide was cleaved from the resin (1.8 g) using 18 mL of HF and 1.8 mL of anisole for 60 min at 0° C. The resin was washed with ether and the peptide extracted with TFA/DCM (1:1, v/v) (3×15 mL) to give 720 mg of crude peptide. The crude linear peptide (500 mg) was dissolved in 80 mL of 50% HOAc and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) the pH was adjusted to 7.5 by addition of NH$_4$OH followed by addition of more K$_3$Fe(CN)$_6$ solution. The total volume of the 0.01M K$_3$Fe(CN)$_6$ solution used for oxidation was 40 mL. An additional 2 mL of K$_3$Fe(CN)$_6$ solution was added extra and the mixture was stirred over 20 min (pH=7.5), then the pH was adjusted to 4–5 by addition of HOAc followed by stirring with 5 g of anion exchange AG 3-X4, 200–400 mesh, free base form (Bio-Rad) over 30 min. The resin was filtered off, washed with 5% acetic acid (3×100 mL) and combined fractions (approx. 1700 mL) were loaded onto a Vydac C-18 column (15μ, 10×30 cm) eluting with 0–15% over 5 min and a 15–55% gradient of 80% ethanol in 0.1% TFA over 55 min at a flow rate of 120 mL per min. Fractions were collected, analyzed by HPLC and pure fractions pooled, evaporated to approx. 100 mL and lyophilized to give 146 mg of white solids. Amino acid analysis: Ala 1.01 (1), Cys 1.60 (2), His 1.03 (1), Leu 2.00 (2), Lys 2.96 (3), Tyr 0.72 (1).

EXAMPLE II

Cyclo-(cystinyl-histidyl-lysyl-leucyl-lysyl-alanyl-alanyl-leucyl-cystinyl)-tyrosine-amide (SEQ ID NO:6)

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.66 g.

The peptide was cleaved from the resin (1.6 g) using 16 mL of HF and 1.6 mL of anisole for 60 min at 0° C. The resin was washed with ether and the peptide extracted with TFA/CH$_2$Cl$_2$ (1:1, v/v) (3×15 mL) to give 748 mg of crude peptide. The crude linear peptide (500 mg) was dissolved in 65 mL of 70% HOAc and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) the pH was adjusted to 7.5 by addition of NH$_4$OH followed by addition of more K$_3$Fe(CN)$_6$ solution. The total volume of the 0.01M K$_3$Fe(CN)$_6$ solution used for oxidation was 30 mL. An additional 2 mL of K$_3$Fe(CN)$_6$ solution was added extra and the mixture was stirred over 20 min (pH=7.5), then the pH was adjusted to 4–5 by addition of HOAc followed by stirring with 5 g of anion exchange AG 3-X4, 200–400 mesh, free base form (Bio-Rad) over 30 min. The resin was filtered off, washed with 5% acetic acid (3×100 mL) and combined fractions (approx. 1700 mL) were loaded onto a Vydac C-18 column (15μ, 10×30 cm) eluting with a 0–15% over 5 min and 15–55% gradient of 80% ethanol in 0.1% TFA over 55 min at a flow rate of 120 mL per min. Fractions were collected, analyzed by HPLC and pure fractions pooled and lyophilized to give 86 mg of white solid. Amino acid analysis: Ala 2.00 (2), Cys 1.55 (2), His 1.00 (1), Leu 2.01 (2), Lys 1.98 (2), Tyr 0.70 (1). Ellman's test for quantitative determination of SH was negative.

EXAMPLE III

Cystinyl-leucyl-lysyl-lysyl-lysyl-histidyl-alanyl-leucyl-cystinyl-tyrosine-amide (SEQ ID NO:1)

The peptide was prepared on an ABI Model 431A Peptide Synthesizer using Version 1.12 of the standard BOC software. 4-methyl benzhdrylamine resin (0.625 g, 0.5 mmol) was used in the synthesis. The final weight of the resin was 1.84 g.

The peptide was cleaved from the resin (1.8 g) using 18 mL of HF and 1.8 mL of anisole for 60 min at 0° C. The resin was washed with ether and the peptide extracted with TFA/CH$_2$Cl$_2$ (1:1, v/v) (3×15 mL) to give 720 mg of crude peptide.

The crude peptide (220 mg) was purified on a Vydac C-18 column (15μ, 5×25 cm) eluting with a 15–45% gradient of 80% acetonitrile in 0.1% TFA over 120 min at a flow rate of 15 mL per min. Fractions were collected, analyzed by HPLC and pure fractions pooled and lyophilized to give 32 mg of white solid. Amino acid analysis: Ala 1.02 (1), Cys 0.88 (2), His 1.06 (1), Leu 1.98 (2), Lys 2.94 (3), Tyr 0.87 (1).

EXAMPLE IV

Cystinyl-histidyl-lysyl-leucyl-lysyl-alanyl-alanyl-leucyl-cystinyl-tyrosine-amide (SEQ ID NO:3)

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.66 g.

The peptide was cleaved from the resin (1.6 g) using 16 mL of HF and 1.6 mL of anisole for 60 min at 0° C. The resin was washed with ether and the peptide extracted with TFA/CH$_2$Cl$_2$ (1:1 v/v) (3×15 mL) to give 748 mg of crude peptide.

The crude peptide (249 mg) was purified in two runs on a Vydac C-18 column (15μ, 5×25cm) eluting with a 5–45% gradient of 80% acetonitrile in 0.1% TFA over 120 min at a flow rate of 15 mL per min. Fractions were collected, analyzed by HPLC and pure fractions pooled and lyophilized to give 53 mg of white solid. Amino acid analysis: Ala 1.97 (2), Cys 0.91, (2), His 1.10 (1), Leu 1.98 (2), Lys 1.95 (2), Tyr 0.74 (1).

EXAMPLE V

Cyclo-(cystinyl-serinyl-lysyl-lysyl-lysyl-leucyl-alanyl-leucyl-cystinyl-tyrosine-amide (SEQ ID NO:5)

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.61 g.

The peptide was cleaved from the resin (1.6 g) using 16 mL of HF and 1.6 mL of anisole for 60 min at 0° C. The resin was washed with ether and the peptide extracted with TFA/CH$_2$Cl$_2$ (1:1, v/v) (3×15 mL) to give 680 mg of crude peptide.

The crude linear peptide (460 mg) was dissolved in 60 mL of 50% HOAc and then added dropwise to the mixture of water (1200 mL), NH$_4$OH (to keep pH approximately 7.5) and 0.01M K$_3$Fe(CN)$_6$ (approximately 3 mL). After each addition of the linear precursor to the reaction mixture (approximately 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 37 mL. The additional 2 mL of K$_3$Fe(CN)$_6$ solution was added extra and the mixture was stirred over 20 min (pH=7.5), then the pH was adjusted to 4–5 by addition of HOAc followed by stirring with 5 g of anion exchange AG 3-X4, 200–400 mesh, free base form (Bio-Rad) over 30 min. The resin was filtered off, washed with 5% acetic acid (3×100 mL) and combined fractions (approximately 1650 mL) were loaded onto a Vydac C-18 column (15μ, 10×30 cm) eluting with a 0–25% over 5 min and 25–55% gradient of 80% ethanol in 0.1% TFA over 55 min at a flow rate of 120 mL per min. Fractions were collected, analyzed by HPLC and pure fractions pooled, evaporated (approximately 100 mL) and lyophilized to give 158 mg of white solid. Amino acid analysis: Ala 1.02 (1), Cys 1.67 (2), Leu 1.99 (2), Lys 2.92 (3), Ser 0.77 (1), Tyr 0.78 (1).

EXAMPLE VI

Cystinyl-serinyl-lysyl-lysyl-lysyl-leucyl-alanyl-leucyl-cystinyl-tyrosine-amide (SEQ ID NO:2)

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.61 g.

The peptide was cleaved from the resin (1.6 g) using 16 mL of HF and 1.6 mL of anisole for 60 min at 0° C. The resin was washed with ether and the peptide extracted with TFA/CH$_2$Cl$_2$ (1:1, v/v) (3×15 mL) to give 680 mg of crude peptide.

The crude peptide (220 mg) was purified on a Vydac C-18 column (15μ, 10×30 cm) eluting with a 0–30% over 5 min and 30–60% gradient of 80% ethanol in 0.1% TFA over 50 min at a flow rate of 120 mL per min. Fractions were collected, analyzed by HPLC and semi-pure fractions pooled, evaporated (approximately 100 mL) and lyophilized to give 66 mg of semi-pure product.

The semi-pure peptide (66 mg) was repurified on a Vydac C-18 column (15μ, 5×25 cm) eluting with a 20–50% gradient of 80% acetonitrile in 0.1% TFA over 120 min at a flow rate of 15 mL/min. Fractions were collected, analyzed by HPLC and pure fractions pooled and lyophilized to give 25 mg of white solid.

Amino acid analysis: Ala 1.00 (1), Cys 1.71 (2), Leu 2.00 (2), Lys 3.00 (3), Ser 0.72 (1), Tyr 0.75 (1).

---

What is claimed is:

1. A peptide capable of inhibiting selectin binding having the formula:

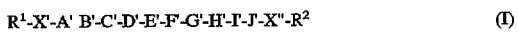

wherein:
- X' is an N-terminus amino acid linear sequence of from zero to 10 amino acids, and $R^1$ is a moiety attached to the terminal α amino group of X', or the terminal α-amino group of the adjacent amino acid if X is zero;
- X" is a C-terminus amino acid linear sequence of from zero to 10 amino acids, and $R^2$ is a moiety attached to the carboxyl carbon of X" or the carboxyl carbon of the adjacent amino acid if X" is zero;
- A' is selected from the group consisting of null (signifying no amino acid) and L-cysteine;
- B' is selected from the group consisting of L-histidine, L-serine, L-leucine, L-phenylalanine, L-asparagine, L-proline, and L-glutamine;
- C' is selected from the group consisting of L-lysine, L-histidine, L-arginine, and L-serine;
- D' is selected from the group consisting of L-lysine, L-leucine, L-alanine, L-phenylalanine, L-histidine, L-arginine, and L-serine;
- E' is selected from the group consisting of L-lysine, L-phenylalanine, L-glutamine, and L-arginine;
- F' is selected from the group consisting of L-histidine, L-leucine, L-alanine, L-isoleucine, L-threonine, and L-arginine;
- G' is selected from the group consisting of L-alanine, L-phenylalanine, L-histidine, L-isoleucine, and L-glutamine;
- H' is selected from the group consisting of L-leucine, L-phenylalanine, L-isoleucine, L-proline, and L-alanine;
- I' is selected from the group consisting of L-cysteine, L-phenylalanine, L-isoleucine, L-histidine, L-leucine, L-valine, L-threonine, and L-serine;
- J' is selected from the group consisting of L-tyrosine, L-phenylalanine, L-isoleucine, and L-valine;
- $R^1$ is selected from the group consisting of hydrogen (signifying a free N-terminal group), lower alkyl, aryl, formyl, alkanoyl, aroyl, alkyloxycarbonyl or aryloxycarbonyl;
- $R^2$ is selected from the group consisting of ON (signifying a free C-terminal carboxylic acid), $OR^3$, signifying ester, where $R^3$ is selected from the group consisting of lower alkyl and aryl; and $NR^5R^6$ where $R^5$ and $R^6$ are each selected independently from hydrogen, lower alkyl, aryl or cyclic alkyl;

and pharmaceutically acceptable salts thereof.

2. The peptide of claim 1 wherein $R^1$ is selected from the group consisting of hydrogen and acetyl.

3. The peptide of claim 1 wherein $R^2$ is selected from the group consisting of ON and $NH_2$.

4. The peptide of claim 3 wherein $R^2$ is $NH_2$.

5. A peptide of claim 1 where $R^1$ is selected from the group consisting of hydrogen and acetyl and $R^2$ is selected from the group consisting of OH and $NH_2$.

6. A peptide of claim 1 wherein, independently, A' is null; B' is selected from the group consisting of Phe, His, Leu, Asn and Ser; C' is selected from the group consisting or Lys and Arg; D' is selected from the group consisting of Lys, Phe, Leu, and Ala; E' is selected from the group consisting of Lys and Arg; F' is selected from the group consisting of Leu and Arg; G' is Ala; H' is Leu; I' is selected from the group consisting of Cys, Ile and Phe; and J' is Tyr.

7. A peptide of claim 6 wherein $R^2$ is $NH_2$.

8. A peptide of claim 1 where E' is Arg.

9. A peptide of claim 7 where E' is Arg.

10. A peptide of claim 1 selected from the group comprising:

(SEQ ID NO:1) Cys-Leu-Lys Lys-Lys-His-Ala-Leu-Cys-Tyr-$NH_2$;
(SEQ ID NO:2) Cys-Ser-Lys-Lys-Lys-Leu-Ala-Leu-Cys-Tyr-$NH_2$;
(SEQ ID NO:3) Cys-His-Lye-Leu-Lys-Ala-Ala-Leu-Cys-Tyr-$NH_2$;
(SEQ ID NO:7) Ac-Phe-Lys-Lys-Lys-Leu-Ala-Leu-Cys-Tyr-$NH_2$;
(SEQ ID NO:8) Phe-Lys-Lys-Lys-Leu-Ala-Leu-Cys-Tyr-$NH_2$;
(SEQ ID NO:9) Ac-His-Lys-Lys-Lys-Leu-Ala-Leu-Cys-Tyr-$NH_2$;
(SEQ ID NO:10) His-Lys-Lys-Lys-Leu-Ala-Leu-Cys-Tyr-$NH_2$;
(SEQ ID NO:11) Leu-Lys-Lys-Lys-His-Ala-Leu-Cys-Tyr-$NH_2$;
(SEQ ID NO:12) Ac-Leu-Lys-Lys-Lys-Leu-Ala-Leu-Cys-Tyr-$NH_2$;
(SEQ ID NO:13) Leu-Lys-Lys-Lys-Leu-Ala-Leu-Cys-Tyr-$NH_2$;
(SEQ ID NO:14) Ac-Asn-Lys-Lys-Lys-Leu-Ala-Leu-Cys-Tyr $NH_2$;
(SEQ ID NO:15) Asn-Lys-Lys-Lys-Leu-Ala-Leu-Cys-Tyr-$NH_2$;
(SEQ ID NO:16) Pro-Lys-Lys-Lys-Leu-Ala-Leu-Cys-Tyr-$NH_2$;
(SEQ ID NO:17) Gln-Lys-Lys-Lys-Leu-Ala-Leu-Cys-Tyr-$NH_2$;
(SEQ ID NO:18) Ser-His-Lys-Lys-Leu Ala-Leu-Cys-Tyr-$NH_2$;
(SEQ ID NO:19) Ac-Ser-Lys-Ala-Lys-Leu-Ala-Leu-Cys-Tyr-$NH_2$;
(SEQ ID NO:20) Ser-Lys-Phe-Lys-Leu-Ala-Leu-Cys-Tyr-$NH_2$;
(SEQ ID NO:21) Ser-Lys-His-Lys-Leu-Ala-Leu-Cys-Tyr-$NH_2$;
(SEQ ID NO:22) Ser-Lys-Lys-Phe-Leu-Ala-Leu-Cys-Tyr-$NH_2$;
(SEQ ID NO:23) Ac-Ser-Lys Lys-Lys-Ala-Ala-Leu-Cys-Tyr-$NH_2$;
(SEQ ID NO:24) Ser-Lys-Lys-Lys-Ala-Ala-Leu-Cys-Tyr-$NH_2$;
(SEQ ID NO:25) Ser-Lys-Lys-Lys-His-Ala-Leu-Cys-Tyr-$NH_2$;
(SEQ ID NO:26) Ser-Lys-Lys-Lys-Ile-Ala-Leu-Cys-Tyr-$NH_2$;
(SEQ ID NO:27) Ser Lys-Lys-Lys-Leu-Ala-Phe-Cys-Tyr-$NH_2$;
(SEQ ID NO:28) Ser-Lys-Lys-Lys-Leu-Ala-Ile-Cys-Tyr-$NH_2$;
(SEQ ID NO:29) Ser-Lys-Lys-Lys-Leu-Ala-Leu-Cys-Phe-$NH_2$;
(SEQ ID NO:30) Ser-Lys-Lys-Lys-Leu-Ala-Leu-Cys-Ile-$NH_2$;
(SEQ ID NO:31) Ser-Lys-Lys-Lys-Leu-Ala-Leu-Cys-Tyr-$NH_2$;
(SEQ ID NO:32) Ser-Lys-Lys-Lys-Leu-Ala-Leu-Phe-Tyr-$NH_2$;

(SEQ ID NO:33) Ser-Lys-Lys-Lys-Leu-Ala-Leu-Ile-Val-NH₂;
(SEQ ID NO:34) Ac-Ser-Lys-Lys-Lys-Leu-Ala-Leu-Ile-Tyr-NH₂;
(SEQ ID NO:35) Ser-Lys-Lys-Lye-Leu-Ala-Leu-Ile-Tyr-NH₂;
(SEQ ID NO:36) Ser-Lys-Lys-Lys-Leu-Ala-Leu-His-Tyr-NH₂;
(SEQ ID NO:37) Ac-Ser-Lys-Lys-Lys-Leu-Ala-Leu-Leu-Tyr-NH₂;
(SEQ ID NO:38) Ser-Lys-Lys-Lys-Leu-Ala-Leu-Leu-Tyr-NH₂;
(SEQ ID NO:39) Ac-Ser-Lys-Lys-Lys-Leu-Ala-Leu-Val-Tyr-NH₂;
(SEQ ID NO:40) Ser-Lys-Lys-Lys-Leu-Ala-Leu-Val-Tyr-NH₂;
(SEQ ID NO:41) Ser-Lys-Lys-Lys-Leu-Ala-Ley-Thr-Tyr-NH₂;
(SEQ ID NO:42) Ser-Lys-Lys-Lys-Leu-Ala-Pro Cys Tyr-NH₂;
(SEQ ID NO:43) Ser-Lys-Lys-Lys-Leu-Phe-Leu-Cys-Tyr-NH₂;
(SEQ ID NO:44) Ser-Lys-Lys-Lys-Leu-His-Leu-Cys-Tyr-NH₂;
(SEQ ID NO:45) Ser-Lys-Lys-Lys-Leu-Ile-Leu-Cys-Tyr-NH₂;
(SEQ ID NO:46) Ser-Lys-Lys-Lys-Leu-Gln-Ala-Cys-Tyr-NH₂;
(SEQ ID NO:47) Ac-Ser-Lys Lys-Lys-Thr-Ala-Leu-Cys-Tyr-NH₂;
(SEQ ID NO:48) Ser-Lys-Lys-Gln-Leu-Ala-Leu-Cys-Tyr-NH₂;
(SEQ ID NO:49) Ac-Ser-Lys-Lys-Arg-Leu-Ala-Leu-Cys-Tyr-NH₂;
(SEQ ID NO:50) Ser-Lys-Lys-Arg-Leu-Ala-Leu-Cys-Tyr-NH₂;
(SEQ ID NO:51) Ac-Ser-Lys-Leu-Lys-Leu-Ala-Leu-Cys-Tyr-NH₂;
(SEQ ID NO:52) Ser-Lys-Leu-Lys-Leu-Ala-Leu-Cys-Tyr-NH₂;
(SEQ ID NO:53) Ac-Ser-Lys-Arg-Lys-Leu-Ala-Leu-Cys-Tyr-NH₂;
(SEQ ID NO:54) Ser-Lys-Arg-Lys-Leu-Ala-Leu-Cys-Tyr-NH₂;
(SEQ ID NO:55) Ac-Ser-Lys-Arg-Lys-Arg-Ala-Leu-Cys-Tyr-NH₂;
(SEQ ID NO:56) Ser-Lys-Arg-Lys-Arg-Ala-Leu-Cys-Tyr-NH₂;
(SEQ ID NO:57) Ac-Ser-Lys-Arg-Arg-Leu-Ala-Leu-Cys-Tyr-NH₂;
(SEQ ID NO:58) Ser-Lys-Arg-Arg-Leu-Ala-Leu-Cys-Tyr-NH₂;
(SEQ ID NO:59) Ser-Lys-Arg-Arg-Leu-Ala-Leu-Ser-Tyr-NH₂;
(SEQ ID NO:60) Ser-Lys-Ser-Lys-Leu-Ala-Leu-Cys-Tyr-NH₂;
(SEQ ID NO:61) Ac-Ser-Arg-Ala-Arg-Leu-Ala-Leu-Cys-Tyr-NH₂;
(SEQ ID NO:62) Ser-Arg-Ala-Ala-Arg-Leu-Ala-Leu-Cys-Tyr NH₂;
(SEQ ID NO:63) Ac-Ser-Arg-Lys-Lys-Leu-Ala-Leu-Cys-Tyr-NH₂;
(SEQ ID NO:64) Ser-Arg-Lys-Lys-Leu-Ala-Leu-Cys-Tyr-NH₂;
(SEQ ID NO:65) Ac-Ser-Arg-Lys-Arg-Leu-Ala-Leu-Cys-Tyr-NH₂;
(SEQ ID NO:66) Ser-Arg-Lys Arg Leu-Ala-Leu-Cys-Tyr-NH₂;
(SEQ ID NO:67) Ser-Arg-Lys-Arg-Leu-Ala-Leu-Ser-Tyr-NH₂;
(SEQ ID NO:68) Ac-Ser-Arg-Arg-Lys-Leu-Ala-Leu-Cys-Tyr-NH₂;
(SEQ ID NO:69) Ser-Arg-Arg-Lys-Leu-Ala-Leu-Cys-Tyr-NH₂;
(SEQ ID NO:70) Ser-Ser-Lys-Lys-Leu-Ala-Leu-Cys-Tyr-NH₂.

11. A pharmaceutical composition comprising at least one peptide of claim 1 in an amount effective to inhibit cellular adherence and a pharmaceutically acceptable carrier or diluent.

12. A method for inhibiting leukocyte adherence in a host comprising the step of administering to said host at least one peptide of claim 1 in an amount effective to inhibit leukocyte adherence.

13. A method for inhibiting cellular adherence in a host comprising administering to said host at least one peptide of claim 1 in an amount effective to inhibit cellular adherence.

14. The method of claim 13 wherein said selectin is selected from the group consisting of P-selectin, E-selectin and L-selectin.

15. A method for decreasing inflammation in a host comprising administering to said host at least one peptide of claim 1 in an amount effective to decrease inflammation.

16. A method of detecting high concentrations or elevated localized concentrations of selectin binding cells and/or integrin binding cells in a host comprising the steps of:

(a) administering to said host a labeled peptide of claim 1;

(b) withdrawing a sample of cells from said host; and (c) assessing the binding of said labeled peptide to said sample of cells.

17. The method of claim 16 wherein said cells are leukocytes.

18. The method of claim 16 wherein said cells are tumor cells.

19. The method of claim 16 wherein said peptide is labeled with a moiety selected from the group consisting of radioactive tracers, fluorescent tags, enzymes, and electron-dense materials.

20. A method of preparing a peptide of claim 1 comprising adding amino acids either singly or in pre-formed blocks of amino acids to an appropriately functionalized solid support.

21. A method of preparing a peptide of claim 1 comprising adding amino acids either singly or in preformed blocks in solution or suspension by chemical ligation techniques.

22. A method of preparing a peptide of claim 1 comprising adding amino acids either singly or in preformed blocks in solution or suspension by enzymatic ligation techniques.

23. A method of preparing a peptide of claim 1 comprising inserting nucleic acids encoding the peptide into an expression vector expressing the DNA, and translating the DNA into the peptide.

* * * * *

UNITED STATES PATENT AND TRADEMARK OFFICE
CERTIFICATE OF CORRECTION

PATENT NO. : 5,710,123
DATED : January 20, 1998
INVENTOR(S) : Heavner et al.

It is certified that error appears in the above-indentified patent and that said Letters Patent is hereby corrected as shown below:

At Column 6, line 21, delete "Ash" and insert -- Asn -- therefor.

At Column 11, line 35, delete "trityl (rrt)" and insert -- trityl (Trt) -- therefor.

At Column 45, line 49, delete "ON" and insert -- OH -- therefor.

At Column 46, line 14, delete "Lye" and insert -- Lys -- therefor.

At Column 47, line 5, delete "Lye" and insert -- Lys -- therefor.

At Column 47, line 59, delete second occurrence of "Ala".

Signed and Sealed this

Twenty-third Day of June, 1998

Attest:

BRUCE LEHMAN

*Attesting Officer*  *Commissioner of Patents and Trademarks*